United States Patent
Abe et al.

(10) Patent No.: US 7,485,719 B2
(45) Date of Patent: Feb. 3, 2009

(54) CROSSLINKABLE POLYSACCHARIDE DERIVATIVE, PROCESS FOR PRODUCING THE SAME, CROSSLINKABLE POLYSACCHARIDE COMPOSITION, AND MEDICAL TREATMENT MATERIAL

(75) Inventors: Yoshihiko Abe, Kanagawa (JP); Takao Anzai, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 122 days.

(21) Appl. No.: 10/546,256

(22) PCT Filed: Feb. 20, 2004

(86) PCT No.: PCT/JP2004/001958

§ 371 (c)(1),
(2), (4) Date: Aug. 19, 2005

(87) PCT Pub. No.: WO2004/081055

PCT Pub. Date: Sep. 23, 2004

(65) Prior Publication Data

US 2006/0178339 A1    Aug. 10, 2006

(30) Foreign Application Priority Data

| Feb. 21, 2003 | (JP) | 2003-044861 |
| Apr. 16, 2003 | (JP) | 2003-111504 |
| Jan. 6, 2004 | (JP) | 2004-001184 |

(51) Int. Cl.
*A61K 31/728* (2006.01)
*C07H 13/10* (2006.01)
*C07H 3/06* (2006.01)

(52) U.S. Cl. ............ 536/123.1; 536/123; 514/54
(58) Field of Classification Search ............ None
See application file for complete search history.

(56) References Cited

U.S. PATENT DOCUMENTS

| 5,676,964 A | 10/1997 | Della Valle et al. |
| 5,874,500 A | 2/1999 | Rhee et al. |
| 5,912,007 A * | 6/1999 | Pan et al. ............ 424/440 |
| 6,083,708 A * | 7/2000 | Singh et al. ............ 435/7.92 |
| 6,312,725 B1 | 11/2001 | Wallace et al. |
| 6,323,278 B2 | 11/2001 | Rhee et al. |
| 6,770,725 B2 * | 8/2004 | Santerre ............ 528/29 |
| 2004/0091540 A1 * | 5/2004 | Desrosiers et al. ............ 424/486 |

FOREIGN PATENT DOCUMENTS

| JP | 89/10941 | 11/1989 |
| JP | 2-504163 | 11/1990 |
| JP | 2002-80501 | 3/2002 |
| JP | 2002-529549 | 9/2002 |
| JP | 2002-529550 | 9/2002 |
| WO | 95/24429 A1 | 9/1995 |

OTHER PUBLICATIONS

Luo et al., "Hyaluronic acid N-Hydroxysuccinimide: A Useful Intermediate for Bioconjugation" Bioconjugate Chemistry (2001) vol. 12, pp. 1085-1088.*
Machine translation of foreign application JP2002-080501 (Jinzo et al.) Translated by the Industrial Property Digital Library at http://www.ipdl.inpit.go.jp/homepg_e.ipdl.*
Zumdahl, S., Chemical Principles, published 1995 by D. C. Health and Company, p. 241.*
J. Milton Harris et al., "Synthesis of New Poly(Ethylene Glycol) Derivatives", Poly(Ethylene Glycol) Chemistry, 1992, pp. 371-381, Department of Chemistry, University of Alabama, Huntsville, AL (cited in specification).
Ronald L. Schnaar et al., "Polyacrylamide Gels Copolymerized With Active Esters, A New Medium for Affinity Systems", Biochemistry, 1975, vol. 14, No. 7, pp. 1535-1541 (cited in specification).

* cited by examiner

*Primary Examiner*—Shaojia Anna Jiang
*Assistant Examiner*—Eric S Olson
(74) *Attorney, Agent, or Firm*—Buchanan Ingersoll & Rooney PC

(57) ABSTRACT

A crosslinkable polysaccharide derivative which has in the side chain of polysaccharide at least one active ester group reactive with an active hydrogen-containing group and which forms a crosslinked product through covalent bond between the active ester group and the active hydrogen-containing group upon contact with alkaline water. A composition and a medical treatment material containing the crosslinkable polysaccharide derivative. The crosslinkable polysaccharide derivative produces a high bond strength that meets clinical requirements. It avoids the risk of infection because it is based on a material which is not derived from living organisms. It in itself and its decomposition products have a low level of toxicity because it is formed from a synthetic material. It is biodegradable and bioabsorbable. It can be prepared readily and simply without requiring special apparatus at the time of use.

4 Claims, No Drawings

CROSSLINKABLE POLYSACCHARIDE DERIVATIVE, PROCESS FOR PRODUCING THE SAME, CROSSLINKABLE POLYSACCHARIDE COMPOSITION, AND MEDICAL TREATMENT MATERIAL

This disclosure is based upon Japanese Application No. 2003-044861, filed Feb. 21, 2003, Japanese Application No. 2003-111504, filed Apr. 16, 2003, Japanese Application No. 2004-001184, filed Jan. 6, 2004, and International Application No. PCT/JP2004/001958, filed Feb. 20, 2004, the contents of which are incorporated herein by reference.

TECHNICAL FIELD

The present invention relates to a crosslinkable polysaccharide derivative to be used under a specific condition, a process for producing the same, a composition containing the polysaccharide derivative, and a medical treatment material based on the composition. More particularly, the present invention relates to a use of a crosslinkable polysaccharide derivative under alkaline conditions which has an active ester group introduced thereinto, and thereby which is capable of self-crosslinking through binding with an intramolecular hydroxy group and is also capable of adhesion to the surface of an organism through binding with an active hydrogen-containing group on the surface of an organism. The present invention relates also to a process for producing a polysaccharide derivative which is essentially with biosafety and chemical safety because of absence of any organism-derived material or any potentially toxic chemical substance, therefore which is a highly biocompatible material. Moreover, the present invention relates also to a crosslinkable polysaccharide composition and a medical treatment material both containing the polysaccharide derivative. Particularly, the medical treatment material is easy to prepare at the time of use, exhibits good adhesion properties to the surface of an organism (as adherend), and forms a flexible crosslinked product which follows easily with a compiant the deformation of the adherend. Hence it is suitable for use as a hemostatic material and a medical adhesive.

BACKGROUND ART

Medical treatment materials play an important role in surgery, reducing time for operation. An example of medical treatment materials is an adhesive for living tissue, which is used to adhere or block vessels or organ tissues to stop leakage of body fluid such as blood, lymph, or gas from sutured or coated tissue.

Among clinically successful and popular adhesives for living tissue is fibrin glue. (See, for example, "Bonding of Living Tissue" by Shojiro Matsuda, "Adhesion" (Japan), vol. 44, No. 1, pp. 19 to 27, Jan. 25, 2000, issued by Kobunshi Kankokai.). Fibrin glue is a two-pack hemostatic material that utilizes the principle of blood coagulation. It works as follows. Fibrinogen is converted into fibrin through the enzymatic action of thrombin. Then, Factor VIII which has been activated by thrombin crosslinks fibrin, thereby forming a fibrin clump. The disadvantage of fibrin glue is the possibility of virus infection through its use, because fibrinogen, Factor VIII, and thrombin constituting fibrin glue are materials derived from living organisms (among organism materials, material from organism such as human and animal) and the quality control for initial material and safety precaution such as inactivation or removal of virus during manufacture are not always complete. Moreover, fibrin glue is expensive, weak in adhesive strength, and complex to handle. Therefore, attempts have been made to find its substitute.

The above-mentioned thesis "Bonding of Living Tissue" also mentions a technique using a gelatin glue (GRF adhesive) as another adhesive for living tissue which has been clinically used with success. GRF is a mixture of gelatin and resorcinol which is to be crosslinked with formaldehyde and glutaraldehyde. It is characterized by high adhesive strength. It is used in the same way as fibrin glue, and it is also used for filling and adhering of a sac resulting from dissecting aneurysm of the aorta. However, it is said to induce a prevention of restoration tissue in the neighborhood of application part because formaldehyde is toxic in itself.

In view of the problems of the biological safety such as infection, in recent years, synthetic material-based tissue adhesives using no material derived from living organisms have been actively developed and some adhesives have been proposed. An example is an ethyl or isobutyl cyanoacrylate adhesive among 2-cyanoacrylate adhesives widely used for the instant adhesive ("Surgery of Stanford Type A Dissecting Aneurysm of Aorta" S. Kawada et al., "Surgical Practice" (Japan), Shindan to Chiryou-sha, vol. 32, No. 9, pp. 1250 to 1258, Sep. 1, 1990). This adhesive is characterized by its rapid adhesion and high adhesion strength because it rapidly polymerizes and cures for adhesion using moisture as a polymerization initiator. However, its cured product is harder than the corresponding living tissue and has no excellent ability to follow the movements of the living tissue. The toxicity problem of formaldehyde generated by the hydrolysis of the cured product in the living organism has also been raised.

One way to obviate these problems is proposed in JP 62-290465 A which describes an adhesive for surgical treatment that includes as a main component an NCO-terminated hydrophilic urethane prepolymer composed of p-phenylene diisocyanate (PPDI) and hydrophilic polyether polyol. In the urethane-based adhesive, first, the isocyanate group at both terminals react with water to generate carbon dioxide gas and to be converted to an amino group. Then, part of the produced amine group react with the isocyanate group and an amino group in living tissue protein also react with the isocyanate group to form urethane linkages, whereby the adhesive is cured to adhere to the living tissue. Since the cured product of the adhesive is flexible, the adhesive is capable of following the movements of living organism. However, the cured product is hardly biodegradable, may cause infection because it remains for a long time and thus has the problem of biodegradability and bioabsorbability.

On the other hand, synthetic tissue adhesives having high adhesion strength and excellent biodegradability and bioabsorbability have also been developed and applied to clinical treatments. An example is a photopolymerizable bioabsorbable adhesive (trade name: Advaseal™), which is mentioned in "Experience in Using Photopolymerizable Absorbable Hydrogel (Advaseal™)—Clinical Application", M. Takagi et al., "Thoracic Surgery" (Japan), Nankodo, vol. 53, No. 11, pp. 951 to 953, Oct. 1, 2000. In this adhesive, acryl ester terminal group is bound to a copolymer of polyethylene glycol (primer) and polylactic acid or a copolymer of polyethylene glycol (primer) and trimethylene carbonate (sealant) and the adhesive also includes an eosin dye as a photosensitive substance. The primer is applied to a wound. Then, the sealant is applied to the wound to which the primer has been applied. Thereafter, the wound is irradiated with light (450 to 550 nm in wavelength) from a xenon light source for about 40 seconds. Irradiation brings about photopolymerization, which causes the preparation to be polymerized and cured into a hydrogel, whereby the preparation adheres to the living tissue. The hydrogel is gradually absorbed into the living body and eventually it disappears about nine months after the application. However, it is necessary to prepare an apparatus for light irradiation on an operating table to use the adhesive, which has a space limitation. The economic burden for the apparatus installation and maintenance is also heavy.

U.S. Pat. No. 6,323,278, JP 2000-502380 and JP 2002-541923 propose other methods in which a two-component mixture type crosslinking material composed of synthetic polymers each having different groups reacting with each other is applied to a tissue to form a crosslinked polymer matrix. More specifically, a first component having a nucleophilic group such as a primary amino group or a thiol group introduced in the molecular chain terminals of polyethylene glycol of a multi-branched structure is mixed with a second component having an electrophilic group such as a succinimidyl group introduced therein to form a crosslinked gel (hydrogel) (U.S. Pat. No. 6,323,278). The polyethylene glycol as the skeleton of each component is one which has a weight-average molecular weight of 10,000, so that the crosslinked product decomposes into small molecules that can be eliminated through kidneys. The adhesive is designed with biodegradation and bioabsorption taken into consideration. However, the two components have to be prepared separately in the form of solution, sprayed through separate ports of an applicator to be mixed together before use and applied to the wound. Therefore, they have to be prepared previously in anticipation of the timing of use during operation. It is difficult to immediately cope with the application.

In the meantime, it is known that polysaccharides are highly biocompatible materials. In particular, U.S. Pat. No. 5,676,964 and WO 00/27886 propose crosslinked products of polysaccharides such as hyaluronic acid having a carboxy group in the molecule. The crosslinked products of polysaccharides are formed by using an intramolecular carboxy group activated by carbodiimide, ethoxyacetylene, Woodward reagent, chloroacetonitrile (U.S. Pat. No. 5,676,964), and an activator used in peptide chemistry (WO 00/27886). For the method of crosslinking activated polysaccharides, are disclosed a crosslinking method by heating or UV light irradiation (U.S. Pat. No. 5,676,964) and a crosslinking method using polyamine (WO 00/27886).

The above-mentioned publications propose the use of the crosslinked products in the form of film, sponge, capsule, tablet, and DDS carrier for medicine and surgery, but do not disclose the use of the activated polysaccharides in uncrosslinked form.

In polysaccharide activation, a carboxy group in the polysaccharide is in the form of salt such as an ammonium salt prior to the reaction with an activator. Inactivated carboxyl residues after the polysaccharide activation are in the form of sodium salt or the like. Therefore, there is a high possibility that the crosslinked product contains residual ammonium or metallic salt.

There is a related art technique (WO 95/24429) which discloses a method of activating a polysaccharide having carboxylic acid in the molecule in the form of salt as mentioned above. It discloses an activated polysaccharide which is formed from a polysaccharide such as hyaluronic acid having a carboxy group in the molecule, by partial or complete esterification with an aromatic alcohol, heteroaromatic alcohol, or N-hydroxylamine alcohol. The activated polysaccharide will find use as an intermediate for peptide synthesis. However, the use of the activated polysaccharide in its uncrosslinked state is not disclosed, as in the above-mentioned patent documents.

As mentioned above, the medical treatment materials typified by tissue adhesives which are used in a living body should meet clinical requirements for not only adhesion strength but also safety, and it is important to design the materials taking into account avoidance of infection by the use of materials not derived from living organism, reduction of the toxicity of the components or a decomposed product by the use of a synthetic material, and biodegradability and bioabsorbability. Moreover, they should be available at any time when necessary without requiring preliminary steps during operation and without requiring special equipment for their use.

DISCLOSURE OF INVENTION

The present invention was completed to realize the medical treatment material that meets the above-mentioned requirements, and this object is achieved by a polysaccharide derivative in a new using manner. It is an object of the present invention to provide a crosslinkable material containing the polysaccharide derivative, a process for producing the same, and a medical treatment material that can be used whenever necessary with simple preliminary steps without requiring special equipment.

The present invention covers the following items (1) to (48).

(1) A crosslinkable polysaccharide derivative for forming a crosslinked product, wherein said crosslinkable polysaccharide derivative has at least one active ester group which has been introduced into the side chain of said polysaccharide and which is reactive with an active hydrogen-containing group, and said crosslinked product has a covalent bond between said active ester group and the active hydrogen-containing group upon contact with water under alkaline conditions.

(2) The crosslinkable polysaccharide derivative according to (1) above, wherein the active hydrogen-containing group is an intramolecular hydroxy group of polysaccharide and said polysaccharide derivative is selfcrosslinkable.

(3) The crosslinkable polysaccharide derivative according to (1) or (2) above, wherein the active hydrogen-containing group is that on the surface of a living organism and the polysaccharide is capable of adhesion to the surface of a living organism.

(4) The crosslinkable polysaccharide derivative according to any one of (1) to (3) above, wherein the active ester group is one in which an electrophilic group attached to a carbonyl group therein.

(5) The crosslinkable polysaccharide derivative according to (4) above, wherein the electrophilic group is one which is introduced from an N-hydroxylamine compound.

(6) A polysaccharide (A) according to any one of (1) to (5) above, wherein the active ester group is a succinimide ester group.

(7) The crosslinkable polysaccharide derivative according to any one of (1) to (6) above, wherein the polysaccharide derivative contains the active ester group in an amount of 0.1 to 2 mmol/g based on dry weight.

(8) The crosslinkable polysaccharide derivative according to any one of (1) to (7) above, wherein the polysaccharide derivative further contains a carboxy group and/or a carboxyalkyl group.

(9) The crosslinkable polysaccharide derivative according to any one of (1) to (8) above wherein the crosslinkable polysaccharide derivative is of non-salt type.

(10) The crosslinkable polysaccharide derivative according to any one of (1) to (9) above, wherein a starting polysaccharide to which to be introduced said active ester group and which has a carboxy group and/or a carboxyalkyl group, as a precursor state of said crosslinkable polysaccharide derivative, is of non-salt form and is a polysaccharide dissoluble in an aprotic polar solvent at a temperature ranging from 60° C. to 120° C.

(11) The crosslinkable polysaccharide derivative according to any one of (1) to (10) above, wherein said starting polysaccharide to be introduced said active ester group thereto is a polysaccharide which does not own a carboxy group and a carboxyalkyl group.

(12) The polysaccharide derivative according to (11) above, wherein the starting polysaccharide is at least one selected from the group consisting of dextran and pullulan.

(13) The polysaccharide derivative according to any one of (1) to (12) above, wherein the starting polysaccharide into which the active ester group is to be introduced is pectin and/or hyaluronic acid. This starting polysaccharide per se is an active esterified precursor (polysaccharide containing an acid group).

(14) The crosslinkable polysaccharide derivative according to any one of (1) to (13) above, wherein pH of the alkaline conditions is ranging from 7.5 to 12.

(15) The crosslinkable polysaccharide derivative according to any one of (1) to (14) above which is in the form of powder.

(16) The crosslinkable polysaccharide derivative according to any one of (1) to (14) above which is in the form of uncrosslinked sheet.

(17) The crosslinkable polysaccharide derivative according to (16) above, wherein the sheet is a heat-dried film or a freeze-dried sheet.

(18) A process for producing a crosslinkable polysaccharide derivative having an active ester group 12. A process for producing a crosslinkable polysaccharide derivative having an active ester group, said process comprises:

dissolving an acid-containing polysaccharides (a precursor of a crosslinkable polysaccharide derivative) having a carboxy group and/or a carboxyalkyl group which are originally possessed or which have been introduced, in its non-salt form, into an aprotic polar solvent at a temperature ranging from 60° C. to 120° C., and reacting it with an electrophilic group-introducing reagent in the presence of a dehydrating-condensing agent, and thereby converting at least part of said carboxy group and/or carboxyalkyl group into active esters.

(19) The process for producing a crosslinkable polysaccharide derivative according to (18) above, wherein the acid-containing polysaccharide contains the carboxy group and/or the carboxyalkyl group in an amount of 0.1 to 5 mmol/g based on dry weight.

(20) The process according to (18) or (19) above, wherein the dehydrating-condensing agent is used in an amount (Z mmol) defined by $0.1<(Z/X)<50$, where X denotes the amount (X mmol) of the carboxy group and/or the carboxyalkyl group in the acid-containing polysaccharide presenting in reaction system.

(21) The process according to any one of (18) to (20) above, which further comprises a step of purifying and/or drying the previously obtained polysaccharide derivative.

(22) The process according to any one of (18) to (21) above, wherein the aprotic polar solvent is dimethylsulfoxide.

(23) The process according to any one of (18) to (22) above, wherein the electrophilic group-introducing reagent is an N-hydroxylamine compound.

(24) The process according to (23) above, wherein the N-hydroxylamine compound is N-hydroxysuccinimide.

(25) The process according to any one of (18) to (24) above, wherein the dehydrating-condensing agent is 1-ethyl-3-dimethyaminopropylcarbodiimide hydrochloride.

(26) The process according to any one of (18) to (25) above, which further comprises steps of preparing an aqueous solution of the previously obtained polysaccharide derivative and developing to form it into an uncrosslinked sheet with desired shape by heat-drying or freeze-drying.

(27) A crosslinkable polysaccharide composition which comprises the crosslinkable polysaccharide derivative (A) according to any one of (1) to (17) above and a polymer (C) other than the polysaccharide derivative (A).

(28) The crosslinkable polysaccharide composition according to (27) above, wherein the polymer (C) is a polymer which has two or more primary amino groups and/or thiol groups in one molecule.

(29) The crosslinkable polysaccharide composition according to (27) or (28) above, wherein the polymer (C) is at least one selected from polyalkylene glycol derivatives, polypeptides, and polysaccharides and derivatives thereof.

(30) The crosslinkable polysaccharide composition according to (29) above, wherein the polyalkylene glycol derivative is at least one selected from the group consisting of polyethylene glycol (PEG) derivative, polypropylene glycol derivative, polybutyrene glycol derivative, and polypropylene glycol-polyethylene glycol block copolymer and random copolymer derivatives.

(31) The crosslinkable polysaccharide composition according to (30) above, wherein the main polymer backbone of the polyethylene glycol derivative is at least one selected from the group consisting of ethylene glycol, trimethylol ethane, diglycerol, pentaerythritol, and hexaglycerol, and has a molecular weight of 100 to 50,000.

(32) The crosslinkable polysaccharide composition according to (30) above, wherein the polyethylene glycol derivative is one which is at least one selected from the group consisting of ethylene glycol-type polyethylene glycol derivative having a thiol group on both terminals and having a weight-average molecular weight of 1,000, 2,000, 6,000, or 10,000, ethylene glycol-type polyethylene glycol derivative having an amino group on both terminals and having a weight-average molecular weight of 1,000, 2,000, 6,000, or 10,000, trimethylol ethane-type polyethylene glycol derivative having a thiol group on three terminals and having a weight-average molecular weight of 5,000 or 10,000, trimethylol ethane-type polyethylene glycol derivative having an amino group on three terminals and having a weight-average molecular weight of 5,000 or 10,000, diglycerol-type polyethylene glycol derivative having a thiol group on four terminals and having a weight-average molecular weight of 5,000, 10,000, or 20,000, diglycerol-type polyethylene glycol derivative having an amino group on four terminals and having a weight-average molecular weight of 5,000, 10,000, or 20,000, pentaerythritol-type polyethylene glycol derivative having a thiol group on four terminals and having a weight-average molecular weight of 10,000 or 20,000, pentaerythritol-type polyethylene glycol derivative having an amino group on four terminals and having a weight-average molecular weight of 10,000 or 20,000, hexaglycerol-type polyethylene glycol derivative having a thiol group on eight terminals and having a weight-average molecular weight of 10,000 or 20,000, and hexaglycerol-type polyethylene glycol derivative having an amino group on eight terminals and having a weight-average molecular weight of 10,000 or 20,000.

(33) The crosslinkable polysaccharide composition according to (29), wherein the polypeptide is at least one selected from the group consisting of collagen, gelatin, albumin, and polylysine.

(34) The crosslinkable polysaccharide composition according to (29), wherein the polysaccharide is at least one selected from the group consisting of pectin, hyaluronic acid, chitin, chitosan, carboxymethylchitin, carboxymethylchitosan, chondroitin sulfate, keratin sulfate, kerato sulfate, heparin, and derivatives thereof.

(35) The crosslinkable polysaccharide composition according to any one of (27) to (34) above, which contains the crosslinkable polysaccharide derivative (A) and the polymer (C) separated in the form of aqueous solution.

(36) The crosslinkable polysaccharide composition according to any one of (27) to (34) above, which is in the form of powder.

(37) The crosslinkable polysaccharide composition according to any one of (27) to (34) above, which is in the form of uncrosslinked sheet.

(38) A sheet-like product according to (37) above, which is a composite sheet comprising a sheet of polysaccharide derivative according to (16) or (17) above and a sheet of the polymer (C) attached thereto.

(39) A method for producing the sheet-like product according to (37) or (38) above, which comprises attaching a sheet of the polymer (C) to an uncrosslinked sheet of the polysaccharide derivative (A) obtained in (26) above.

(40) The method for producing the sheet-like product according to (39) above, wherein the polymer (C) is dissolved in a nonaqueous volatile organic solvent and the resulting solution is impregnated into the uncrosslinked sheet-like product of the polysaccharide derivative (A) and dried.

(41) A crosslinkable polysaccharide composition which includes the polysaccharide derivative (A) according to any one of (1) to (17) above and a pH adjusting agent (B) which is not mixed with the polysaccharide derivative (A).

(42) The crosslinkable polysaccharide composition according to any one of (27) to (35) above, which further includes a pH adjusting agent (B) which is not mixed with the polysaccharide derivative (A).

(43) The crosslinkable polysaccharide composition according to (35) above, wherein the aqueous solution of the polymer (C) contains the pH adjusting agent (B).

(44) A medical treatment material which comprises either the crosslinkable polysaccharide derivative according to any one of (1) to (17) above or the crosslinkable polysaccharide composition according to any one of (27) to (43) above.

(45) The medical treatment material according to (44) above, which is a hemostatic material and/or a biomedical adhesive.

(46) The medical treatment material according to (44) or (45) above, which is in the form of aerosol or paste.

(47) A kit which includes the medical treatment material according to any one of (44) to (46) above.

(48) A method for restraining hemostasis and/or adhering of living organism, which comprises reacting either the crosslinkable polysaccharide derivative according to any one of (1) to (17) above or the crosslinkable polysaccharide composition according to any one of (27) to (43) above at a desired part in the presence of water under alkaline conditions.

The polysaccharide derivative according to the present invention is essentially with biosafety and chemical safety and hence highly biocompatible in itself because it is not based on any organism-derived material or potentially toxic chemical substance. Moreover, since the polysaccharide derivative is self-crosslinkable and capable of adhesion to the surface of a living organism under alkaline conditions, and can be easily prepared at the time of use without requiring any special equipment, and may sufficiently adhere to the surface of a living organism and forms a crosslinked product which is flexible enough to follow the deformation of adherent, it is suitable for use as a medical treatment material such as a hemostatic material or a biomedical adhesive.

BEST MODE FOR CARRYING OUT THE INVENTION

A detailed description is given below of the crosslinkable polysaccharide derivative, the crosslinkable polysaccharide composition and the medical treatment material containing it, and the process for producing them according to the present invention.

The crosslinkable polysaccharide derivative of the present invention has at least one active ester group, which has been introduced into the side chain of the polysaccharide, and which is reactive with an active hydrogen-containing group. The polysaccharide (the starting material) to which to be introduced the active ester group will be described later, the polysaccharide molecule originally has an hydroxy group i.e. an active hydrogen-containing group, therefore, the polysaccharide having the active ester group introduced thereto has both the active ester group and the active hydrogen-containing group in one molecular chain and is self-crosslinkable under the reaction conditions. The self-crosslinking means an intramolecular or intermolecular reaction between an active ester group and an active hydrogen-containing group of the polysaccharide derivative to form the covalent bond. In a case of utilizing an active hydrogen-containing group on the surface of living organism, the crosslinkable polysaccharide derivative may adhere to the surface of living organism.

In this specification, such crosslinkable polysaccharide derivative mentioned above may be referred to as active esterified polysaccharide or simply polysaccharide derivative herein after.

Incidentally, the term molecule used in "one molecular chain" or "intramolecular" means one molecule consisting of one region connected with serial bonds by covalent bond.

The polysaccharide derivative of the present invention is an active esterified polysaccharide, and essentially retains the skeleton of polysaccharide. Therefore, the polysaccharide derivative will be described below together with the active-esterifying method (the process for producing the polysaccharide derivative).

In the present invention, the active ester group to be introduced into the polysaccharide is not specifically restricted so long as it forms covalent bond upon reaction with an active hydrogen-containing group in the presence of water under alkaline conditions. This active ester group is a group in which an electrophilic group stronger than an ordinary ester bound to the carbonyl carbon of a carboxy group or a methylcarboxy group which is ordinarily owned by the polysaccharide or introduced upon conversion into acid type. To be concrete, the active ester group may be represented by —COOX, —OX representing the alcohol moiety is from the electrophilic group which is preferably a group introduced from an N-hydroxylamine compound. The N-hydroxylamine compound is a comparatively inexpensive raw material and hence it is easy in operation for introduction of the active ester group on an industrial scale.

The N-hydroxylamine compound to form the —OX moiety includes, for example, N-hydroxysuccinic imide, N-hydroxynorbornene-2,3-dicarboxylic imide, ethyl ester of 2-hydroxyimino-2-cyanoacetate, 2-hydroxyimino-2-cyanoacetic amide, and N-hydroxypiperidine.

In the present invention, the active ester group in the polysaccharide derivative may have one or more species.

Of these active ester groups, the succinimide ester group is desirable.

The polysaccharide derivative of the present invention has at least one active ester group mentioned above in the molecule, however, generally, it has two or more active ester groups in the molecule so that it forms the crosslinked matrix. The amount of the active ester group per one gram of polysaccharide derivative based on dry weight should preferably be 0.1 to 2 mmol/g, which varies depending on the purpose of use.

In the present invention, the polysaccharide constituting the main skeleton of the polysaccharide derivative, having the active ester group introduced thereinto, is not specifically restricted so long as it has two or more units of monosaccharide structure in the main skeleton. Such polysaccharides include those formed through covalent bond from monosaccharides such as arabinose, ribose, xylose, glucose, mannose, galactose, fructose, sorbose, rhamnose, furcose, and ribodesose; disaccharides such as trehalose, sucrose, maltose, cellobiose, gentiobiose, lactose, melibiose; and tri or more polysaccharides such as raffinose, gentianose, merezitose, and stachyose; those having further functional groups introduced thereinto. In the present invention, such polysaccharide may be naturally occuring ones or artificially synthesized ones. Also, the polysaccharide derivative of the present invention may have the skeleton of one polysaccharide or two or more polysaccharides.

The polysaccharide constituting the main skeleton of the polysaccharide derivative of the present invention is not specifically restricted in weight-average molecular weight. It should preferably have a weight-average molecular weight of 5,000 to 2,500,000, which corresponds to that of a polysaccharide composed of tens to thousands of monosaccharides, disaccharides, or tri or more, and polysaccharides mentioned above. Such a polysaccharide gives rise to a gel (which results from the polysaccharide derivative of the present invention through crosslinking) that permits easy adjustment of hardness, because it also permits easy introduction of more than one active ester group and active hydrogen-containing group into one molecular chain. A desirable polysaccharide is one which has a weight-average molecular weigh of 10,000 to 1,000,000.

The starting polysaccharide constituting the main skeleton of the polysaccharide derivative should preferably be a polysaccharide having the above constituent, which has a carboxylic acid group to form the active ester group"— COOX" in the precursor state prior to active esterification (It may be referred to as an acid group-containing polysaccharide hereinafter.). The carboxylic acid group denotes a carboxy group and/or carboxyalkyl group (which may be collectively referred to as a carboxylic acid group hereinafter). The carboxyalkyl group is a functional group in which carboxy group binds to the alkyl skeleton, as which includes carboxymethyl group, carboxyethyl group, carboxypropyl group, carboxyisopropyl group, and carboxybutyl group.

The above-mentioned starting polysaccharide is not specifically restricted so long as it is an acid group-containing polysaccharide in the precursor state of the crosslinkable polysaccharide derivative. It may be a native polysaccharide having a carboxylic acid. It may also be a polysaccharide which does not originally have a carboxylic acid but has a carboxy group and/or carboxyalkyl group introduced thereinto. Of these carboxylic acid group-containing polysaccharides, the following are desirable. Natural polysaccharide having a carboxy group. Carboxylated polysaccharide having a carboxy group introduced thereinto. Carboxymethylated polysaccharide having a carboxymethyl group introduced thereinto. Carboxyethylated polysaccharide having a carboxyethyl group introduced thereinto. The following are particularly desirable. Natural polysaccharide having a carboxy group, carboxylated polysaccharide having a carboxy group introduced therein, and carboxymethylated polysaccharide having a carboxymethyl group introduced thereinto.

The above-mentioned native polysaccharide having a carboxylic acid is not specifically restricted. It includes pectin (which contains galacturonic-acid) and hyaluronic acid. Pectin is commercially available under a trade name of "GENUE Pectin" from CP Kelco (Denmark) and hyaluronic acid is commercially available under a trade name of "Hyaluronic acid FCH" from Kibun Food Inc. (Japan). Pectin is a polysaccharide composed mainly of galacturonic acid (about 75 to 80%), the remainder being other sugars. In other words, pectin is a polysaccharide composed of galacturonic acid and other sugars in the above-mentioned ratio. Hyaluronic acid is used for ophthalmic surgery adjuvant and therapy eutic agent of degenerative osteoarthrosis. Hyaluronic acid does not contain galacturonic acid.

In the present invention, the carboxy group and/or carboxyalkyl group in the polysaccharide derivative is preferably "non-salt" type; in other words non-coordinated salt, and, it is desirable that the finally resulting polysaccharide derivative is not in the form of salt. The term "salt" includes inorganic salt of alkali metal or alkaline earth metal, quaternary amine salt such as tetrabutyl ammonium (TBA), and halogenate salt such as chloromethyl pyridilium iodide. The term "non-salt" type means that the derivative does not have such a "salt". The term "not in the form of salt" means that the derivative does not contain such a salt.

The polysaccharide into which to be introduced the above-mentioned carboxy group and/or carboxyalkyl group are, but is not specifically restricted, may include dextran and pullulan.

Dextran is used as a blood plasma substitute. Dextran may include "Dextran T fractions" from Amersham Biosciences (Japan), and Pullulan may include "Pullulan PI-20" from Hayashibarashasha (Japan). Pullulan is used as a medical adjuvant including an oral medication. Preferable one is free of biological contamination such as endotoxin.

In the present invention, any one which is commercially available in general may be used for each polysaccharide. Those polysaccharides which have been used for therapy as mentioned above are suitable for use in the present invention from the view point of safety.

The carboxylation reaction of polysaccharide may be accomplished by any known oxidation reaction without specific restrictions. Type of carboxylation reaction, but is not specifically restricted, includes oxidation with dinitrogen tetraoxide, oxidation with fusing sulfuric acid, oxidation with phosphoric acid, oxidation with nitric acid, and oxidation with hydrogen peroxide. Each oxidation with the reagent will be accomplished by selecting the reaction known in ordinary. The condition of reaction may be properly established depending on the amount of carboxy group to be introduced. For example, a carboxylated polysaccharide (a carboxylated form of polysaccharide) may be prepared through the oxidation of the hydroxy group in a polysaccharide by suspending a polysaccharide as a starting material into chloroform or carbon tetrachloride and adding a dinitrogen tetraoxide thereto.

Additionally, a carboxylalkylation reaction may be accomplished by any known carboxyalkylation reaction of polysaccharide, but is not specifically restricted, typically in the case of carboxymethylation, may be applied of the reaction which uses monochloroacetic acid after alkalifying of polysaccharide. The condition of reaction may be properly established depending on the amount of carboxymethyl group to be introduced.

In the present invention, it is possible to employ either the carboxylation or the carboxyalkylation mentioned above as a method for introducing the carboxylic acid group into a polysaccharide, but is not limited, carboxyalkylation, especially carboxymethylation is suitable because it does not appreciably reduce the molecular weight of polysaccharide after introduction of the carboxy group and it permits easy control over the amount of the carboxy group to be introduced.

In the present invention, introduction of the carboxylic acid group is not restricted to polysaccharide which does not originally have the carboxylic acid group. Introduction of carboxy group and/or carboxymethyl group may be performed on native polysaccharide, such as hyaluronic acid mentioned above, which originally has the carboxylic acid group.

One or more than one acid group-containing polysaccharide may be used to active-esterify the carboxy group and/or carboxymethyl group therein.

The acid group-containing polysaccharide to be active-esterified should be one which contains carboxylic acid group (regarded as one molecule) in an amount of usually 0.1 to 5 mmol/g, preferably 0.4 to 3 mmol/g, more preferably 0.6 to 2 mmol/g (on dry basis). If the amount of carboxylic acid group is less than 0.1 mmol/g, it is often the case that there will be an insufficient number of active ester group for forming a crosslinking point derivated therefrom. If the amount of carboxylic acid group is more than 5 mmol/g, the polysaccharide (uncrosslinked) is poorly soluble in a water-containing solvent.

The method of active-esterifying the acid group-containing polysaccharide (the method for producing the polysaccharide derivative) is not specifically restricted. It may be the one which involves reacting the acid group-containing polysaccharide with an electrophilic group-introducing agent in the presence of a dehydrating-condensing agent, or it may be the one which involves ester exchange reaction to introduce an active ester group into the polysaccharide from a compound having an active ester group. The former method is suitable for the present invention, and this method will be described in the following. (It will be referred to as the method of the present invention.)

The method of the present invention is accomplished usually by dissolving the acid group-containing polysaccharide in an aprotic polar solvent and using the resulting solution for reaction. To be concrete, the method comprises a step of dissolving a polysaccharide having a carboxy group or a carboxyalkyl group in an aprotic polar solution, thereby preparing a solution, a step of adding to the solution an electrophilic group-introducing agent and a dehydrating-condensing agent, thereby active-esterifying the carboxy group or carboxyalkyl group of the polysaccharide, and a step of purifying and drying the reaction product.

In the solution preparing step, the polysaccharide is added to a solvent, and heated at 60 to 120° C., so that the polysaccharide is dissolved in an aprotic polar solvent.

Consequently, the acid group-containing polysaccharide to be active-esterified should preferably be one among the above listed polysaccharides which is soluble in an aprotic polar solvent at a temperature in the range of 60° C. to 120° C. To be concrete, the polysaccharide to be used for the reaction for introduction of electrophilic group should preferably be one in which the carboxy group or the acid type carboxymethyl group is, from the standpoint of solubility in the aprotic polar solvent. The term "acid type" means that the species of counter cation of the carboxy group or the carboxymethyl group is proton. The polysaccharide which has an acid type carboxy group is referred to as acid type (starting) polysaccharide. For example, pectin as a polysaccharide having a carboxy group is referred to as acid type pectin. Carboxymethyl dextran having acid type carboxymethyl group is referred to as acid type carboxymethyl (CM) dextran or acid type CM dextran. The term "acid type" has the same meaning as the "non-salt type" mentioned above in the sense that the species of counter cation is proton, and is in the form of "non-salt".

The "aprotic polar solvent" denotes a polar solvent which does not have proton capable of forming hydrogen bond with a nucleophilic agent having an electrically positive functional group. The aprotic polar solvent that can be used in the method of the present invention is not specifically restricted; it includes, for example, dimethylsulfoxide (DMSO), N,N-dimethylformamide, N-methyl-2-pyrolidone, N,N-dimethylacetamide, and 1,3-dimethyl-2-imidazoline. Of these examples, dimethylsulfoxide may be used preferably because of its dissolibility to polysaccharide.

In the reaction step, to the solution of acid type polysaccharide is added the electrophilic group-introducing agent and the dehydrating-condensing agent so as to active-esterify the carboxy group and/or the carboxymethyl group in the polysaccharide. The reaction temperature for active-esterification is not specifically restricted; it is preferably 0° C. to 70° C., more preferably 20° C. to 40° C. The reaction time varies depending on the reaction temperature; it is usually 1 to 48 hours, preferably 12 to 24 hours.

The "electrophilic group-introducing agent" refers to a regent which introduces an electrophilic group into the carboxy group or the carboxyalkyl group, thereby converting it into an active ester group. The electrophilic group-introducing agent is not specifically restricted; it may be a compound for introduction of active ester, which is generally used for peptide synthesis. It includes, for example, N-hydroxylamine-based compound for introduction of active ester. The N-hydroxylamine-based compound for introduction of active ester is not specifically restricted; it includes, for example, N-hydroxysuccinimide, N-hydroxynorbornene-2,3-dicarboxylic imide, ethyl ester of 2-hydroxyimino-2-cyanoacetate, 2-hydroxyimino-2-cyanoacetic amide, and N-hydroxypiperidine. Of these examples, N-hydroxysuccinimide is desirable because it is commercially available and has been widely used in the field of peptide synthesis.

The "dehydrating-condensing agent" is one that withdraws one water molecule, dehydrates in other word, which occurs by condensation between the carboxy group or carboxyalkyl group and the electrophilic group-introducing agent when the carboxy group or carboxyalkyl group is converted into the active ester group by the electrophilic group-introducing agent, thereby forming an ester linkage between them. The dehydrating-condensing agent is not specifically restricted; it includes, for example, 1-ethyl-3-dimethylaminopropylcarbodiimide hydrochloride (EDC.HCl) and 1-cyclohexyl-(2-morphonyl-4-ethyl)-carbodiimide-meso-p-toluenesulfonate. Of these examples, 1-ethyl-3-dimethylaminopropylcarbodiimide hydrochloride (EDC.HCl) is desirable because it is commercially available and has been widely used in the field of peptide synthesis.

The purifying step comprises ordinary reprecipitation (from reaction liquid), filtration, and/or washing, which are carried out after the reaction is complete. By the purifying step, was removed the electrophilic group-introducing agent and dehydrating-condensing agent remaining unreacted and by-products, thereby was obtained the polysaccharide derivative of the present invention.

The drying step may be carried out by a commonly used method to remove a washing solvent from the polysaccharide derivative obtained in the purifying step.

According to the present invention, the amount of the active ester group in the polysaccharide derivative which is eventually obtained should preferably be 0.1 to 2 mmol/g, as mentioned above. In the above-mentioned steps, it is possible to control the amount of active ester group to be introduced into the carboxy group of the starting polysaccharide for active esterification so that the desired polysaccharide derivative is obtained.

In order to control the amount of active ester group to be introduced, it is possible to adjust the mixing amounts of the electrophilic group-introducing agent and the dehydrating condensation agent in the above-mentioned reaction steps. More specifically, the addition condition that the ratio (Z/X) of the number of moles (Z mmol) of the dehydrating condensation agent to the number of moles (X mmol) of total carboxy group in the polysaccharide is 0.1<Z/X<50 is preferably used. If the ratio Z/X is smaller than 0.1, the reaction efficiency is low because of a small amount of the dehydrating condensation agent added. Therefore, it is difficult to achieve a desired active ester group-introducing ratio. If the ratio Z/X is larger than 50, a high active ester group-introducing ratio is achieved because of a larger amount of the dehydrating condensation agent but the resulting polysaccharide is hardly soluble in water.

The number of moles of the electrophilic group-introducing agent (Y mol) to the number of moles of total carboxy group in the polysaccharide is not specifically restricted so long as the electrophilic group-introducing agent and the dehydrating condensation agent are added in amounts equal to or larger than the reaction amounts corresponding to the active ester group introducing-ratio. However, the addition condition satisfying 0.1<Y/X<100 is preferably used.

The polysaccharide derivative according to the present invention usually retains the hydroxy group of the glucopyranose ring in its skeleton molecule even after the active ester group have been introduced therein. Therefore, the polysaccharide derivative has the active hydrogen-containing group. The active hydrogen-containing group in the molecule are not limited thereto and the polysaccharide may additionally have active hydrogen-containing groups introduced in the molecule as required. In this case, the polysaccharide derivative may have one kind or more than one kind of active hydrogen-containing group.

In addition to the above-mentioned active ester group and active hydrogen-containing group, the polysaccharide derivative of the present invention may contain any known elements, atomic groups, or other functional groups in the amounts that do not adversely affect the merits of the present invention.

Examples of the functional group include halogen elements such as fluorine, chlorine, bromine, and iodine, carboxy group, carboxyalkyl groups such as carboxymethyl group, carboxyethyl group, carboxypropyl group, and carboxyisopropyl group, silyl group, alkylenesilyl group, alkoxysilyl group, and phosphate group. These functional groups may be used alone or in combination of two or more.

The active ester group-introducing ratio (%) can be represented by multiplying by 100 a ratio (AE/TC) of the molar amount of the active ester group in the resulting polysaccharide derivative (AE) to the molar amount of the carboxy group in the starting polysaccharide for the active esterification and the molar amount of the carboxymethyl group (hereinafter referred to as total carboxy group (TC).

The active ester group-introducing ratio can be determined by, for example, the method described in Biochemistry vol. 14, No. 7 (1975), pp. 1535 to 1541.

In particular, the polysaccharide derivative may include residual carboxy group and/or carboxymethyl group from the starting polysaccharide has when the active ester group are introduced at an active ester group-introducing ratio of less than 100%.

The term "crosslinked structure" means a three-dimensional network structure of the molecular chains of the polysaccharide derivative which is formed through covalent bond within one molecular chain and/or between two or more molecular chains of the polysaccharide derivative of the present invention. The active ester group and the active hydrogen-containing group may be bound together within one molecular chain through crosslinking, but crosslinking may be formed through covalent bond between two or more molecules. The polysaccharide derivative of the present invention is water-soluble before it is crosslinked. However, when the reaction progresses, it forms a crosslinked structure, which reduces flowability to produce water-insoluble aggregated matrix (water-containing gel), whereby a crosslinked polysaccharide is formed. The polysaccharide derivative of the present invention is a self-crosslinkable polysaccharide. The term "self-crosslinkable" is defined as the property of forming the crosslinked structure through covalent bond within its own molecule or between molecular chains without particularly using other crosslinking agent.

The polysaccharide derivative of the present invention exhibits not only the self-crosslinking property in which intramolecular active hydrogen-containing group is involved but also the adhesiveness to the surface of living organism through reaction of the active hydrogen-containing group on the surface of the living organism with the active ester group, if it is applied to the surface of the living organism. This mode of use is desirable for the polysaccharide derivative of the present invention. The self-crosslinking may also be formed when the polysaccharide derivative is applied to the surface of the living organism.

According to the present invention, the active hydrogen-containing group involved in the reaction with the active ester group is not specifically restricted so long as it is a group that may form covalent bond through reaction with the active ester group under specified conditions in the present invention. Any active hydrogen-containing group can also be used in the present invention. Specific examples include hydroxy group, amino group, and thiol group. Examples of the amino group include primary amino group and secondary amino group. Of these, the case where the active hydrogen-containing group is hydroxy group or primary amino group is preferable because of excellent reactivity with the active ester group and short time for crosslinking to gelation.

The method of crosslinking the polysaccharide derivative of the present invention refers to a method of forming covalent bond through reaction between the active ester group and the active hydrogen-containing group. Specific examples include a method in which the polysaccharide derivative of the present invention is crosslinked under alkaline conditions in the presence of moisture such as water, water vapor, or water-containing solvent, and a method in which a pH adjusting agent is added to a polysaccharide derivative solution for crosslinking.

To be more specific, it is possible to crosslink the polysaccharide derivative in the presence of water at a pH of 7.5 to 12, preferably 9.0 to 10.5. If the pH of the water is lower than 7.5, self-crosslinking property is low and a sufficient degree of crosslinking is not obtained. On the other hand, even if crosslinking progresses at a pH of 12 or more, this is not appropriate considering the physiological conditions.

The term "alkaline conditions" used in the present invention means the condition under which moisture having a pH of 7.5 or more is present. The "alkaline conditions" is not specifically restricted in temperature; but the temperature can be set for example in a range of 10° C. to 40° C., because heat does not greatly contribute to the crosslinking of the crosslinkable polysaccharide derivative of the present invention.

The term "brought into contact with water under alkaline conditions" means that the polysaccharide derivative is brought into contact with moisture in any form under alkaline conditions to place it under alkaline conditions. When the polysaccharide derivative is in powder form, it is possible to add water adjusted to alkaline conditions or to add water to a mixture of the polysaccharide derivative powder with a pH adjusting agent. When the polysaccharide derivative is in the form of aqueous solution, it is possible to add water previously adjusted to alkaline conditions or to add a pH adjusting agent. These operations place the polysaccharide derivative in an alkaline environment, and the crosslinking reaction starts. In other words, the polysaccharide derivative starts crosslinking upon contact with moisture under alkaline conditions and the crosslinking progresses. Therefore, the mixture of the polysaccharide derivative and water under alkaline conditions may have a pH under alkaline conditions, but the alkaline condition is not obligatory. The polysaccharide derivative begins to crosslink upon contact with water under alkaline conditions, but crosslinking reaction does not substantially start or proceed by exposure to UV light or by heating.

In the present invention, the polysaccharide derivative mentioned above can be provided as a crosslinkable material only composed of the polysaccharide derivative for its self-crosslinking property. A crosslinkable material in the form of a composition composed of a combination with other components can also be provided. Depending on the type, other components may be added to form a composition in contact with the polysaccharide derivative or may not be in contact therewith until they are mixed together before use.

The polysaccharide derivative can be provided in the form of powder or sheet. In other words, the polysaccharide derivative in powder form can be obtained by crushing or grinding the polysaccharide derivative prepared by the above-mentioned synthesis and optionally adjusting the particle size. There is no particular limitation to reduce the particle size, but freeze grinding, milling and/or classification may be performed after crushing or grinding, the particle size can also be adjusted by sieving to have any particle size distribution. The average particle size is not specifically restricted; however, it should preferably be tens of nanometers to hundreds of micrometers. The resulting powder may be made into paste or aerosol by a commonly used method.

The polysaccharide derivative in sheet form can be prepared by a solution preparing step in which the polysaccharide derivative is dissolved in water and a drying step in which the solution is spread out into a desired shape and heat-dried or freeze-dried. To be more specific, the polysaccharide derivative in sheet form can be obtained by preparing an aqueous solution in which the polysaccharide derivative is dissolved and freeze-drying the aqueous solution. When the polysaccharide derivative in sheet form is prepared, it is desirable that the water used for preparing the aqueous solution have a pH of 3.0 to 7.5. If the water has a pH of not more than 3.0, the resulting sheet exhibits strong acidity. If the water has a pH of 7.5 or more, the active ester group is often released. The heat-dried sheet can be obtained by spreading the aqueous solution on a substrate and then heat-drying it at 30° C. to 110° C. If necessary, heat-drying may be accomplished under reduced pressure. The freeze-dried sheet can be obtained by freezing the aqueous solution and then drying it in its frozen state. If necessary, freeze-drying may be accomplished by using an ordinary freeze-drier.

The present invention provides a crosslinkable polysaccharide composition containing the polysaccharide derivative (A) and the pH adjusting agent (B) as a composition containing the above-mentioned polysaccharide derivative (A). This composition can be used as an adhesive or glue.

The pH adjusting agent (B) may be supplied without being mixed or after having previously been mixed. The period when the pH adjusting agent (B) is mixed is not specifically restricted, but the period is appropriately selected from before use and during use. The composition including the polysaccharide derivative (A) and the pH adjusting agent (B) may optionally contain any other substances. Such other substances may or may not be mixed with the polysaccharide derivative.

The pH adjusting agent (B) used in the present invention denotes an aqueous solution, a water-containing solvent, or salt (powder) for adjusting the polysaccharide derivative or the crosslinkable polysaccharide composition of the present invention to a pH of 7.5 to 12. The pH adjusting agent (B) is not specifically restricted. Specific examples include sodium hydrogencarbonate in the form of aqueous solution or powder, phosphate buffer (disodium hydrogenphosphate and potassium dihydrogenphosphate), and acetic acid-ammonia buffer. Of these, sodium hydrogencarbonate can be suitably used from the viewpoint of safety in that its 7% aqueous solution (pH 8.3) of sodium hydrogencarbonate is used as a pH adjusting agent for medical purposes in the form of intravenous injection.

The above-mentioned composition may be in two-component type, with one being an aqueous solution containing 1 to 80% (w/v) of the polysaccharide derivative and the other being water adjusted to a pH of 7.5 to 10.5.

The two components can be mixed together before use to obtain an aqueous solution having a final polysaccharide derivative concentration of 0.1 to 60% (w/v). Alternatively, it is possible to add a salt of the pH adjusting agent (B) to an aqueous solution having a polysaccharide derivative concentration of 1 to 80% (w/v) before use and dissolve the salt therein to obtain a mixture having a final polysaccharide derivative concentration of 0.1 to 80% (w/v). Mixing may be accomplished in a conventional mixing method, but it is preferable to mix to a homogenous state. The resulting mixture should be homogenous enough to permit a desired reaction to proceed.

The present invention also provides the crosslinkable polysaccharide composition (also abbreviated as polysaccharide composition) which contains the polysaccharide derivative (A) and another polymer (C). The polymer (C) is used to adjust the hardness and other properties of hydrogel which is formed when the polysaccharide composition is crosslinked. The polysaccharide derivative (A) may be used alone or in combination of two or more. The pH adjusting agent (B) may also be contained in the composition.

The polymer (C) is not specifically restricted, but it is preferable to use one which has more than one primary amino group, thiol group, or hydroxy group in one molecule. Specific examples of the polymer (C) include polyalkylene glycol derivative, polypeptide, polysaccharide, and a derivative thereof. The content of the polymer (C) in the polysaccharide composition of the present invention is not specifically restricted, but it should preferably be 5 to 50 wt % based on the total amount of the polysaccharide composition. The polymer (C) can be used alone or in combination of two or more.

The polyalkylene glycol derivative mentioned above includes, for example, polyethylene glycol (PEG) derivative, polypropylene glycol derivative, polybutylene glycol derivative, and polypropylene glycol-polyethylene glycol block copolymer derivative and random copolymer derivative. The polyethylene glycol derivative has the main polymer backbone of ethylene glycol, diglycerol, pentaerythritol, or hexaglycerol. The polyalkylene glycol derivative should preferably have a molecular weight of 100 to 50,000, more preferably 1,000 to 20,000.

The polyethylene glycol mentioned above is not specifically restricted; it includes, for example, ethylene glycol-type polyethylene glycol derivative having a thiol group on both terminals and having a weight-average molecular weight of 1,000, 2,000, 6,000, or 10,000, ethylene glycol-type polyethylene glycol derivative having an amino group on both terminals and having a weight-average molecular weight of 1,000, 2,000, 6,000, or 10,000, trimethylol ethane-type polyethylene glycol derivative having a thiol group on three terminals and having a weight-average molecular weight of 5,000 or 10,000, trimethylol ethane-type polyethylene glycol derivative having an amino group on three terminals and having a weight-average molecular weight of 5,000 or 10,000, diglycerol-type polyethylene glycol derivative having a thiol group on four terminals and having a weight-average molecular weight of 5,000, 10,000, or 20,000, diglycerol-type polyethylene glycol derivative having an amino group on four terminals and having a weight-average molecular weight of 5,000, 10,000, or 20,000, pentaerythritol-type polyethylene glycol derivative having a thiol group on four terminals and having a weight-average molecular weight of 10,000 or 20,000, pentaerythritol-type polyethylene glycol derivative having an amino group on four terminals and having a weight-average molecular weight of 10,000 or 20,000, hexaglycerol-type polyethylene glycol derivative having a thiol group on eight terminals and having a weight-average molecular weight of 10,000 or 20,000, and hexaglycerol-type polyethylene glycol derivative having an amino group on eight terminals and having a weight-average molecular weight of 10,000 or 20,000.

The term "weight-average molecular weight" is a numerical value that represents the average molecular weight of a polymer. Since a polymer is a mixture of molecules having the same main structural units but differing in the length of molecules (or chains), it has a distribution of molecular weight according to the lengths of molecules. To indicate the molecular weight, the average molecular weight is used. The average molecular weight may be represented in terms of weight-average molecular weight, number-average molecular weight or the like. Here, the weight-average molecular weight is used. In the present invention, the value (100%) of the weight-average molecular weight embraces the one whose upper limit is 110% and whose lower limit is 90%. The polyethylene glycol derivative may be prepared by the process mentioned in Poly (ethylene glycol) Chemistry: Biotechnical and Biomedical Applications, compiled by J. Milton Harris, issued by Plenum Press, NY (1992), Chapter 22. It may also be chemically modified such that it contains one or more than one primary amino group or thiol group. Also, the polyethylene glycol derivative is commercially available from NOF Corporation under the trade names of Sunbrite HGEO-20TEA, Sunbrite PTE-10TSH or the like.

The polypeptide mentioned above is not specifically restricted; it includes, for example, collagen, gelatin, albumin, and polylysine. The polysaccharide is not specifically restricted; it includes, for example, pectin, hyaluronic acid, chitin, chitosan, carboxymethylchitin, carboxymethylchitosan, chondroitin sulfate, keratin sulfate, kerato sulfate, and heparin, and derivatives thereof.

The polysaccharide composition of the present invention, which is composed of the polysaccharide derivative (A) (active esterified polysaccharide) and the polymer (C), should preferably have the following combination of (A) and (C). The form (sheet, powder, liquid) for each combination will be properly selected with reference to Examples mentioned later.

Combination of active esterified pectin with at least one polymer (C) selected from the group consisting of ethylene glycol-type PEG derivative having a thiol group on both terminals, ethylene glycol-type PEG derivative having an amino group on both terminals, trimethylol ethane-type PEG derivative having a thiol group on three terminals, trimethylol ethane-type PEG derivative having an amino group on three terminals, pentaerythritol-type PEG derivative having a thiol group on four terminals, pentaerythritol-type PEG derivative having an amino group on four terminals, hexaglycerol-type PEG derivative having a thiol group on eight terminals, hexaglycerol-type PEG derivative having an amino group on eight terminals, albumin, gelatin, collagen, polylysine, pectin, chitosan, chitin, and carboxymethyl (CM) chitin.

Combination of active esterified CM dextran with at least one polymer (C) selected from the group consisting of ethylene glycol-type PEG derivative having a thiol group on both terminals, ethylene glycol-type PEG derivative having an amino group on both terminals, trimethylol ethane-type PEG derivative having a thiol group on three terminals, trimethylol ethane-type PEG derivative having an amino group on three terminals, pentaerythritol-type PEG derivative having a thiol group on four terminals, pentaerythritol-type PEG derivative having an amino group on four terminals, hexaglycerol-type PEG derivative having a thiol group on eight terminals, hexaglycerol-type PEG derivative having an amino group on eight terminals, albumin, gelatin, collagen, polylysine, pectin, chitosan, chitin, and CM chitin.

Combination of active esterified CM pullulan with at least one polymer (C) selected from the group consisting of ethylene glycol-type PEG derivative having a thiol group on both terminals, ethylene glycol-type PEG derivative having an amino group on both terminals, trimethylol ethane-type PEG derivative having a thiol group on three terminals, trimethylol ethane-type PEG derivative having an amino group on three terminals, pentaerythritol-type PEG derivative having a thiol group on four terminals, pentaerythritol-type PEG derivative having an amino group on four terminals, hexaglycerol-type PEG derivative having a thiol group on eight terminals, hexaglycerol-type PEG derivative having an amino group on eight terminals, albumin, gelatin, collagen, polylysine, pectin, chitosan, chitin, and CM chitin.

Combination of active esterified CM hydroxyethyl starch with at least one polymer (C) selected from the group consisting of ethylene glycol-type PEG derivative having a thiol group on both terminals, ethylene glycol-type PEG derivative having an amino group on both terminals, trimethylol ethane-type PEG derivative having a thiol group on three terminals, trimethylol ethane-type PEG derivative having an amino group on three terminals, pentaerythritol-type PEG derivative having a thiol group on four terminals, pentaerythritol-type PEG derivative having an amino group on four terminals, hexaglycerol-type PEG derivative having a thiol group on eight terminals, hexaglycerol-type PEG derivative having an amino group on eight terminals, albumin, gelatin, collagen, polylysine, pectin, chitosan, chitin, and CM chitin.

Combination of active esterified pectin with at least one polymer (C) selected from the group consisting of ethylene glycol-type PEG derivative having a thiol group on both terminals and having a weight-average molecular weight of 1,000, 2,000, 6,000, or 10,000, ethylene glycol-type PEG derivative having an amino group on both terminals and having a weight-average molecular weight of 1,000, 2,000, 6,000, or 10,000, trimethylol ethane-type PEG derivative having a thiol group on three terminals and having a weight-average molecular weight of 5,000 or 10,000, trimethylol ethane-type PEG derivative having an amino group on three terminals and having a weight-average molecular weight of 5,000 or 10,000, diglycerol-type PEG derivative having a thiol group on four terminals and having a weight-average molecular weight of 5,000, 10,000, or 20,000, diglycerol-type PEG derivative having an amino group on four terminals and having a weight-average molecular weight of 5,000, 10,000, or 20,000, pentaerythritol-type PEG derivative having a thiol group on four terminals and having a weight-average molecular weight of 10,000 or 20,000, pentaerythritol-type PEG derivative having an amino group on four terminals and having a weight-average molecular weight of 10,000 or 20,000, hexaglycerol-type PEG derivative having a thiol group on eight terminals and having a weight-average molecular weight of 10,000 or 20,000, and hexaglycerol-type PEG derivative having an amino group on eight terminals and having a weight-average molecular weight of 10,000 or 20,000.

Combination of active esterified CM dextran with at least one polymer (C) selected from the group consisting of ethylene glycol-type PEG derivative having a thiol group on both terminals and having a weight-average molecular weight of 1,000, 2,000, 6,000, or 10,000, ethylene glycol-type PEG derivative having an amino group on both terminals and having a weight-average molecular weight of 1,000, 2,000, 6,000, or 10,000, trimethylol ethane-type PEG derivative having a thiol group on three terminals and having a weight-average molecular weight of 5,000 or 10,000, trimethylol ethane-type PEG derivative having an amino group on three terminals and having a weight-average molecular weight of 5,000 or 10,000, diglycerol-type PEG derivative having a thiol group on four terminals and having a weight-average molecular weight of 5,000, 10,000, or 20,000, diglycerol-type PEG derivative having an amino group on four terminals and having a weight-average molecular weight of 5,000, 10,000, or 20,000, pentaerythritol-type PEG derivative having a thiol group on four terminals and having a weight-average molecular weight of 10,000 or 20,000, pentaerythritol-type PEG derivative having an amino group on four terminals and having a weight-average molecular weight of 10,000 or 20,000, hexaglycerol-type PEG derivative having a thiol group on eight terminals and having a weight-average molecular weight of 10,000 or 20,000, and hexaglycerol-type PEG derivative having an amino group on eight terminals and having a weight-average molecular weight of 10,000 or 20,000.

Combination of active esterified pullulan with at least one polymer (C) selected from the group consisting of ethylene glycol-type PEG derivative having a thiol group on both terminals and having a weight-average molecular weight of 1,000, 2,000, 6,000, or 10,000, ethylene glycol-type PEG derivative having an amino group on both terminals and having a weight-average molecular weight of 1,000, 2,000, 6,000, or 10,000, trimethylol ethane-type PEG derivative having a thiol group on three terminals and having a weight-average molecular weight of 5,000 or 10,000, trimethylol ethane-type PEG derivative having an amino group on three terminals and having a weight-average molecular weight of 5,000 or 10,000, diglycerol-type PEG derivative having a thiol group on four terminals and having a weight-average molecular weight of 5,000, 10,000, or 20,000, diglycerol-type PEG derivative having an amino group on four terminals and having a weight-average molecular weight of 5,000, 10,000, or 20,000, pentaerythritol-type PEG derivative having a thiol group on four terminals and having a weight-average molecular weight of 10,000 or 20,000, pentaerythritol-type PEG derivative having an amino group on four terminals and having a weight-average molecular weight of 10,000 or 20,000, hexaglycerol-type PEG derivative having a thiol group on eight terminals and having a weight-average molecular weight of 10,000 or 20,000, and hexaglycerol-type PEG derivative having an amino group on eight terminals and having a weight-average molecular weight of 10,000 or 20,000.

Combination of active esterified CM hydroxyethyl starch with at least one polymer (C) selected from the group consisting of ethylene glycol-type PEG derivative having a thiol group on both terminals and having a weight-average molecular weight of 1,000, 2,000, 6,000, or 10,000, ethylene glycol-type PEG derivative having an amino group on both terminals and having a weight-average molecular weight of 1,000, 2,000, 6,000, or 10,000, trimethylol ethane-type PEG derivative having a thiol group on three terminals and having a weight-average molecular weight of 5,000 or 10,000, trimethylol ethane-type PEG derivative having an amino group on three terminals and having a weight-average molecular weight of 5,000 or 10,000, diglycerol-type PEG derivative having a thiol group on four terminals and having a weight-average molecular weight of 5,000, 10,000, or 20,000, diglycerol-type PEG derivative having an amino group on four terminals and having a weight-average molecular weight of 5,000, 10,000, or 20,000, pentaerythritol-type PEG derivative having a thiol group on four terminals and having a weight-average molecular weight of 10,000 or 20,000, pentaerythritol-type PEG derivative having an amino group on four terminals and having a weight-average molecular weight of 10,000 or 20,000, hexaglycerol-type PEG derivative having a thiol group on eight terminals and having a weight-average molecular weight of 10,000 or 20,000, and hexaglycerol-type PEG derivative having an amino group on eight terminals and having a weight-average molecular weight of 10,000 or 20,000.

The ratio of the polysaccharide derivative (A) (SD) to the polymer (C) (AP) should preferably be SD/AP=20/80 to 98/2 (w/w). If the amount of the polymer (C) is more than 80 wt %, the polysaccharide derivative (A) hardly exhibits its self-crosslinking property. If the amount of the polymer (C) is less than 2 wt %, it will be difficult to control the hardness and other properties of the hydrogel to be obtained eventually.

The polysaccharide composition of the present invention may be incorporated with various kinds of known additives in an amount not harmful to the effect of the present invention. The additives are not specifically restricted; they include cure catalyst, filler, plasticizer, softener, stabilizer, dehydrizer, coloring agent, anti-sag agent, thickener, property adjusting agent, reinforcing agent, thixotropic agent, age resistor, flame retardant, antioxidant, UV light absorber, pigment, solvent, carrier, shaping agent, antiseptic, binder, antioxidant, swelling agent, isostatic agent, solubilizing agent, preservative, buffer solution, and diluent. These additives may be used alone or in combination with one another.

The polysaccharide composition mentioned above may be provided in the form of sheet, powder, or liquid. The polysaccharide composition in powder form may be prepared by mixing the polysaccharide derivative (A) in powder form mentioned above with the polymer (C) in powder form. The polysaccharide composition in powder form mentioned may also be mixed with a salt of pH adjusting agent in powder form to give the polysaccharide composition containing a salt of pH adjusting agent.

The above-mentioned polysaccharide composition in powder form or the above-mentioned polysaccharide composition in powder form containing a salt of pH adjusting agent may be made into granules by granulation. The above-mentioned polysaccharide composition in powder form or the above-mentioned polysaccharide composition in powder form containing a salt of pH adjusting agent may also be made into sheet or plate by compression. The polysaccharide composition in sheet form may be obtained by attaching the polymer (C) in powder form or by impregnating with the polymer (C) by coating, to the heat-dried or freeze-dried sheet of the above-mentioned polysaccharide derivative (A). The term "impregnating" means that the surface of the sheet is impregnated with the polymer (C) so that the surface of the sheet is covered with the polymer (C). In the case where the sheet is of porous structure, "impregnating" means that the polymer (C) covers the sheet surface and the pores' internal surface inside of the sheet.

The polysaccharide composition may be of two-pack type, which consists of an aqueous solution of the polysaccharide derivative (A) and an aqueous solution of the polymer (C). Upon mixing of these two aqueous solutions, there is obtained a hydrogel consisting of the polysaccharide derivative (A) and the polymer (C). The aqueous solution of the polysaccharide derivative (A) should preferably have a concentration of 1 to 80% (w/v), and the aqueous solution of the polymer (C) should preferably have a concentration of 1 to 80% (w/v). The polymer (C) may be dissolved in water adjusted to pH 7.5 to 10.5 or in pure water or buffer solution which is incorporated with a salt of pH adjusting agent at the time of mixing. After the aqueous solutions of the polysaccharide derivative (A) and the polymer (C) have been mixed together, the total concentration of the polysaccharide derivative (A) and the polymer (C) in the mixed solution should preferably be 0.1 to 80% (w/v).

The polysaccharide composition in sheet crosslinks when used in the presence of water. Water may be the above-mentioned pH adjusting agent. The pH adjusting agent should preferably be an aqueous solution adjusted to pH 7.5 to 10.5. The pH adjusting agent in power form may be attached to the polysaccharide composition in sheet form.

The polysaccharide composition in sheet form can be prepared by dissolving the polysaccharide derivative (A) in water, spreading the resulting aqueous solution into a desired shape, drying the spread solution, and impregnating the polymer (C) to the polysaccharide derivative (A) in sheet form thus obtained. The impregnating step may be accomplished by dipping the sheet in the polymer (C) and a solution containing a non-aqueous volatile organic solvent, followed by drying. In this way it is possible to impregnate the polymer (C) without impairing the surface shape of the polysaccharide derivative (A) in sheet form. Incidentally, the term "non-aqueous volatile organic solvent" means any water-incompatible volatile organic solvent. The non-aqueous volatile organic solvent is not specifically restricted; it includes chloroform and dichloromethane.

The polysaccharide derivative of the present invention and the polysaccharide composition containing it may be used in a desired form as a medical treatment material. The term "medical treatment material" means any substance which is composed of components safe and acceptable (with a low level of toxicity) to the living body when used in the living body. It may or may not be biodegradable in the living body. It should preferably be biodegradable in the living body. For example, it may be used for hemostasis, adhesion, sealing, and/or fixing of the tissue or organ during operation. The medical treatment material is not specifically restricted in form; it may be in the form of sheet, powder, paste, or aerosol.

The medical treatment material may be used in the form of mixture with the above-mentioned pH adjusting agent. The medical treatment material may be mixed with the pH adjusting agent previously or in situ at the time of use. The medical treatment material may be applied to the desired spot after incorporation with an aqueous solution of the pH adjusting agent or the like at the time of use.

As in the case of the polysaccharide composition of the present invention, the medical treatment material may also be incorporated with various kinds of known additives, preferably compatible with the living body, in an amount not harmful to the effect of the present invention. The additives are not specifically restricted; they include carrier, shaping agent, antiseptic, stabilizer, binder, antioxidant, swelling agent, isostatic agent, solubilizing agent, preservative, buffer solution, and diluent. These additives may be used alone or in combination of two or more.

The additives are exemplified by water, physiological saline, organic solvent for medicinal use, gelatin, collagen, polyvinyl alcohol, polyvinyl pyrrolidone, carboxyvinyl polymer, sodium carboxymethylcellulose, sodium polyacrylate, sodium alginate, water-soluble dextran, sodium carboxymethyl starch, pectin, methyl cellulose, ethyl cellulose, xanthan gum, gum Arabic, tragacanth, casein, agar, diglycerin, propylene glycol, polyethylene glycol, petrolatum, paraffin, stearyl alcohol, stearic acid, human blood serum albumin (HSA), mannitol, sorbitol, lactose, PBS, nonionic surfactant, biodegradable polymer, serum-free culture medium, surfactants acceptable for use as pharmaceutical additive, and buffer solution with a physiological pH suitable for living bodies.

The carrier may be properly selected alone or in combination from the foregoing according to the wound for application. However, the carriers are not restricted to those mentioned above. The medical treatment material may be prepared into gel or aerosol (in combination with an adequate propellant).

The medical treatment material may be provided in the form of kit containing the above-mentioned pH adjusting agent for convenience at the time of use. The medical treatment material in the form of kit includes the polysaccharide derivative (A), the polysaccharide composition, and/of the pH adjusting agent, which are not mixed together. They are contained all together or separately in one package. The medical treatment material may contain any other constituents which can be used as medical treatment material.

The kit may contain the polysaccharide derivative or polysaccharide composition in the form of powder, sheet, or aqueous solution which may or may not contain the pH adjusting agent in the form of aqueous solution or powder.

The medical treatment material may be used as a hemostatic and/or adhesive. The hemostatic is used to stop bleeding in a living body. To this end, the medical treatment material is applied to the bleeding wound. The medical treatment material is applied to a target portion and covers the bleeding portion as required to stop bleeding and thus achieve the hemostatic effect. The adhesive is used to bond at least one part of the living tissue or organ to the other part. To this end, the medical treatment material is applied to the desired spot and allowed to stand under pressure (or without pressure) for a certain period of time. Upon the above process, it is possible to use a fixing tool or the like.

The polysaccharide derivative or the polysaccharide composition, which is in the form of power, sheet, or aqueous solution containing or not containing the pH adjusting agent in the form of aqueous solution or powder, may be contained in the hemostatic and/or adhesive.

The medical treatment material of the present invention is used as a hemostatic and/or adhesive. Consequently, the present invention offers a method of stopping bleeding and/or bonding living organism by brining the medical treatment material into contact with a desired spot in the presence of water. The object is achieved by spraying, filling, or coating the medical treatment material in powder form. For the medical treatment material in sheet form, the object is achieved by pasting, filling, covering, pressing, and allowing to stand. For the medical treatment material in liquid form, the object is achieved by applying, spraying, dropping, and rubbing. In this way it is possible to achieve hemostasis and/or adhesion.

The polysaccharide derivative of the present invention has an active ester group and an active hydrogen-containing group in one molecular chain, so that they react with each other to form a covalent bond, thereby forming the crosslinked structure. When used as an adhesive, it produces sufficient tissue bond strength that meets the clinical requirements and it avoids risk of infection because it does not use any material originating from living tissue but it is based on natural or artificial polysaccharide for the backbone. Its components or their decomposition products have a low level of toxicity and are capable of biodegradation and bioabsorption because the backbone is formed from polysaccharide. The polysaccharide derivative of the present invention does not need complex steps for preparation at the time of use. It can be prepared readily and simply without requiring special apparatus at the time of use. The polysaccharide derivative may be provided alone or as the polysaccharide composition; therefore, it will find a large variety of uses. Since the polysaccharide composition of the present invention employs the polysaccharide derivative of the present invention having the property described above, it does not impair the characteristic properties of the present invention.

The polysaccharide derivative and polysaccharide composition of the present invention can be fabricated into powder, sheet, granules, or any other forms. Therefore, they can be used in various ways according to the object of their use. The polysaccharide derivative and polysaccharide composition of the present invention can be produced simply by mixing with heating necessary reagents, without requiring special apparatus. Owing to the above-mentioned characteristic properties, the polysaccharide derivative and polysaccharide composition of the present invention are suitable for use as the medical treatment material such as hemostatic agent and adhesive.

EXAMPLES (I) Preparation of Starting Polysaccharide

An acid group-containing polysaccharide that is a polysaccharide having an acid-type carboxy group or an acid-type carboxymethyl group was prepared as a starting polysaccharide to be a starting material for the active esterified polysaccharide (polysaccharide derivative) of the present invention.

(1) Preparation of Acid-type Pectin

Five grams of pectin (GENU Pectin USP-H from CP Kelco) was suspended in 500 mL of 90 vol % methanol aqueous solution (100% methanol from Wako Pure Chemical Industries, Ltd.). The resulting suspension was adjusted to pH 1.0 with 20% hydrochloric acid (hydrochloric acid from Wako Pure Chemical Industries, Ltd.). After stirring at 25° C. for 2 hours, the suspension was filtered through a suction funnel to recover pectin. The recovered pectin was washed with 2 liters of 80 vol % methanol aqueous solution, and finally washed with 100% methanol, and vacuum dried. Consequently, an acid-type pectin was obtained.

(2) Preparation of Acid-type Hyaluronic Acid

An acid-type hyaluronic acid was prepared in the same way as in (I)-(1) except that the pectin used in (I)-(1) was replaced by sodium hyalronate (Hyaluronic acid FCH-150 from Kibun Food Inc.).

(3) Preparation of Acid-type Carboxymethyldextran A (Acid-type CM Dextran A)

Twenty grams of dextran (Dextran T-40 from Amercham Biosciences, having a weight-average molecular weight of 40,000) was dissolved in 75 mL of pure water. To the resulting solution was added 50 mL of 45% (w/v) sodium hydroxide aqueous solution (sodium hydroxide from Wako Pure Chemical Industries, Ltd.). The resulting solution was stirred at 25° C. for 2 hours. Then, 75 mL of 40% (w/v) aqueous solution of monochloroacetic acid (monochloroacetic acid from Wako Pure Chemical Industries, Ltd.), and the resulting solution was stirred at 25° C. for 18 hours. The reaction liquid was adjusted to pH 1.0 with 20% hydrochloric acid, followed by stirring at 25° C. for 2 hours. The reaction liquid was added dropwise to 5 L of 90 vol % ethanol aqueous solution (100% ethanol from Wako Pure Chemical Industries, Ltd.). Precipitates were recovered by filtration through a suction funnel. The recovered precipitates were washed with 3 L of 90 vol % ethanol aqueous solution, finally, washed with ethanol. Upon drying in vacuo, there was obtained the acid-type CM dextran A.

(4) Preparation of Acid-type CM Dextran B

An acid-type CM dextran B was prepared in the same way as in (I)-(3) except that the dextran (20 g) used in (I)-(3) was replaced by dextran having a different molecular weight (Dextran T-500 from Amersham Biosciences, having a weight-average molecular weight of 500,000).

(5) Preparation of Acid-type Carboxymethyl Pullulan (Acid-type CM Pullulan)

An acid-type CM pullulan was prepared in the same way as in (I)-(3) except that the dextran (20 g) used in (I)-(3) was replaced by 10 g of pullulan (PI-20, from Hayashibarasha).

(II) Quantitative Determination of Carboxy Group or Carboxymethyl Group

Quantitative determination of carboxy group or carboxymethyl group was performed for the starting polysaccharide obtained in (I)-(1) to (I)-(5). 0.2 g (A g) of the starting polysaccharide was weighed, and dissolved in a mixed solution composed of 20 mL of aqueous solution of sodium hydroxide (0.1 mol/L) and 10 mL of aqueous solution of methanol (80 vol %), followed by stirring at 25° C. for 3 hours. Three drops of 1.0% (w/v) phenolphthalein solution in 90 vol % ethanol (as an indicator) were added to the solution (Phenolphthalein from Wako Pure Chemical Industries, Ltd.). An acid-base back titration was performed by using 0.05 mol/L sulfuric acid, and the amount used of 0.05 mol/L sulfuric acid (V1 mL) was determined. In blank test in the same way except adding the starting polysaccharide, the amount of spent 0.05 mol/L sulfuric acid (V0 mL) was determined. The amount (B mmol/g) of carboxy group and carboxymethyl group in the starting polysaccharide was calculated from the following equation. Incidentally, both the 0.1 mol/L aqueous solution of sodium hydroxide and the 0.05 mol/L sulfuric acid have a titer of 1.00. The results are shown in Table 1 below.

$$B=(V_0-V_1)\times 0.1 \div A \qquad (1)$$

where,

A: mass of starting polysaccharide (g)
B: amount of carboxy group and carboxymethyl group (mmol/g)

TABLE 1

| Acid-type starting polysaccharide | Amount of carboxy group and carboxymethyl group (mmol/g) |
|---|---|
| Pectin | 1.40 |
| Hyaluronic acid | 2.15 |
| CM dextran A | 1.01 |
| CM dextran B | 0.29 |
| CM pullulan | 1.28 |

(III) Preparation of Active Esterified Polysaccharide (Polysaccharide Derivative)

An active esterified polysaccharide (polysaccharide derivative) was prepared by the above-mentioned active esterification reaction of the acid-type starting polysaccharide, in which DMSO as the reaction medium, N-hydroxysuccinimide (NHS) (from Wako Pure Chemical Industries, Ltd.) as the electrophilic group-introducing agent, and 1-ethyl-3-dimethylaminopropylcarbodiimide hydrochloride (EDC) (from Wako Pure Chemical Industries, Ltd.) as the dehydrating-condensing agent were used.

Example 1

Preparation of Active Esterified Pectin

In 200 g of DMS was added 2.0 g of acid-type pectin (containing 1.40 mmol/g of carboxy group) prepared in (I)-(1), and dissolved by stirring at 25° C. for 15 hours. The resulted solution was added 0.322 g (2.80 mmol) of NHS and 0.536 g (2.80 mmol) of EDC, followed by stirring at 25° C. for 24 hours. The reaction solution was dropped into 2 L of anhydrous acetone (from Wako Pure Chemical Industries, Ltd.), and a precipitate was recovered by filtration through a suction funnel. The precipitate was washed with 1 L of anhydrous acetone, followed by vacuum drying. Thus the active esterified pectin was obtained. Incidentally, the ratios of Z/X and Y/X were as follows:

$Z/X=1.0$ and $Y/X=1.0$

Example 2

Preparation of Active Esterified Hyaluronic Acid

In 200 g of DMS was added 2.0 g of acid-type hyaluronic acid (containing 2.15 mmol/g of carboxy group) prepared in (I)-(2), and dissolved by stirring at 25° C. for 15 hours. The resulting solution was added 0.575 g (5.0 mmol) of NHS and 0.958 g (5.0 mmol) of EDC, followed by stirring at 25° C. for 24 hours. The reaction solution was dropped into 2 L of diethyl ether (from Wako Pure Chemical Industries, Ltd.), and precipitate was recovered by filtration through a suction funnel. The precipitate was washed with 1 L of tetrahydrofuran (from Wako Pure Chemical Industries, Ltd.), followed by vacuum drying. Thus the active esterified hyaluronic acid was obtained. Incidentally, the ratios of Z/X and Y/X were as follows:

$Z/X=1.0$ and $Y/X=1.0$

Example 3

Preparation of Active Esterified CM Dextran A1

In 200 g of DMS was added 2.0 g of acid-type dextran A (containing 1.01 mmol/g of carboxymethyl group) prepared in (I)-(3), and dissolved by stirring at 100° C. for 15 hours. The resulting solution was added 2.325 g (20.2 mmol) of NHS and 1.162 g (6.06 mmol) of EDC, followed by stirring at 25° C. for 24 hours. The reaction solution was dropped into 2 L of anhydrous acetone, and precipitate was recovered by filtration through a suction funnel. The precipitate was washed with 1 L of anhydrous acetone, followed by vacuum drying. Thus the active esterified CM dextran A1 was obtained. Incidentally, the ratios of Z/X and Y/X were as follows:

$Z/X=3.0$ and $Y/X=10$

Example 4

Preparation of Active Esterified CM Dextran A2

The same procedure as in (I)-(3) was repeated except that 1,162 g (6.06 mmol) of EDC was changed to 1.936 g (10.1 mmol) of EDC to give the active esterified CM dextran A2. Incidentally, the ratios of Z/X and Y/X were as follows:

$Z/X=5.0$ and $Y/X=10$

Example 5

Preparation of Active Esterified CM Dextran A3

The same procedure as in (I)-(3) was repeated except that 1.162 g (6.06 mmol) of EDC was changed to 2.325 g (20.2 mmol) of EDC to give the active esterified CM dextran A2. Incidentally, the ratios of Z/X and Y/X were as follows:

$Z/X=10$ and $Y/X=10$

Example 6

Preparation of Active Esterified CM Dextran B

In 200 g of DMS was added 2.0 g of acid-type dextran B (containing 0.29 mmol/g of carboxymethyl group) prepared in (I)-(4), and dissolved by stirring at 100° C. for 15 hours. The resulting solution was added 1.12 g (5.8 mmol) of NHS and 0.333 g (2.06 mmol) of EDC, followed by stirring at 25° C. for 24 hours. The reaction solution was dropped into 2 L of anhydrous acetone, and precipitates were recovered by filtration through a suction funnel. The precipitate was washed with 1 L of anhydrous acetone, followed by vacuum drying. Thus the active esterified CM dextran B was obtained. Incidentally, the ratios of Z/X and Y/X were as follows:

$Z/X=5.0$ and $Y/X=10$

Example 7

Preparation of Active Esterified CM Pullulan

In 200 g of DMS was added 2.0 g of acid-type CM pullulan (containing 1.28 mmol/g of carboxymethyl group) prepared in (I)-(5), and dissolved by stirring at 100° C. for 15 hours. The resulting solution was added 0.294 g (2.56 mmol) of NHS and 0.491 g (2.56 mmol) of EDC, followed by stirring at 25° C. for 24 hours. The reaction solution was dropped into 2 L of anhydrous acetone, and precipitate was recovered by filtration through a suction funnel. The precipitate was washed with 1 L of anhydrous acetone, followed by vacuum drying. Thus the active esterified CM pullulan obtained. Incidentally, the ratios of Z/X and Y/X were as follows:

$Z/X=0.5$ and $Y/X=1.0$ (IV) Calculation of the NHS-introducing Ratio of Active Esterified Polysaccharide (Polysaccharide Derivative)

The NHS-introducing ratio was calculated for the active esterified polysaccharide (polysaccharide derivative) prepared in Examples 1 to 7 in (III). The NHS-introducing ratio is defined as the ratio of the amount of active ester group in the resulting polysaccharide derivative to the amount of carboxy group or carboxymethyl group in a unit by weight of the starting polysaccharide to be the raw material for the polysaccharide derivative.

In order to make a calibration curve for N-hydroxysuccinimide (NHS), 0.1, 0.2, 0.5, 1.0, 2.5, 5.0, and 10 mM of NHS standard aqueous solutions were prepared. To 1 mL of each standard aqueous solution of NHS was added 0.2 mL of 2N aqueous solution of sodium hydroxide, followed by stirring at 60° C. with heating for 10 minutes. After standing to cool, 1.5 mL of 0.85 N hydrochloric acid and 0.75 mL of 0.05% $FeCl_3$/1 N hydrochloric acid solution were added, followed by measuring for absorbance at a wavelength of 500 nm by using a spectrophotometer ($FeCl_3$ from Wako Pure Chemical Industries, Ltd.). The concentration of each aqueous solution of NHS on the X axis, and the absorbance on the Y axis were plotted and then linearised, and consequently the equation (2) to calculate the concentration of NHS was obtained as follows.

$$Y = \alpha X + \beta \quad (2)$$

where,
X: concentration of NHS (mM)
Y: absorbance at a wavelength of 500 nm
α=0.102 (gladient)
β=0.0138 (intercept)
r=0.991 (correlation coefficient)

The content (C mmol) of NHS group in the sample below mentioned can be obtained by multiplying the value of X (mM) calculated from the absorbance by the volume (3.45 mL) of the solution used for measurement.

Next, 0.01 g of the active esterified polysaccharide prepared in Examples 1 to 7 was weighed and added in 1 mL of pure water, followed by stirring at 25° C. for 3 hours, and then 0.2 mL of 2 N aqueous solution of sodium hydroxide was added thereto, followed by stirring at 60° C. for 10 minutes. After cooling to the room temperature, 1.5 mL of 0.85 N hydrochloric acid was added. The resulting solution which includes insolubles was filtered through filter cotton to remove insolubles, and was measured for absorbance at a wavelength of 500 nm, after 0.75 mL of 0.05% $FeCl_3$ solution in 1 N hydrochloric acid was added thereto. If the measured absorbance was higher than that obtained when the concentration of the NHS standard solution was 5 mM, the solution was diluted with pure water. (The dilution ratio H.) The content (C mmol) of NHS group in the active esterified polysaccharide was calculated from the measured absorbance by using the equation (2) to calculate the concentration of NHS. And then, the NHS-introducing ratio of the active esterified polysaccharide was determined by using the equation (3) below. The results are shown in Table 2.

$$NHS\text{-introducing ratio }(\%) = \{(C \times H)/0.01\}/B \times 100 \quad (3)$$

where,
B: The total amount of carboxy group in the starting polysaccharide for an active esterified polysaccharide (mmol/g)
C: The amount of NHS group in an active esterified polysaccharide (mmol)

TABLE 2

| | Acid-type starting poly-saccharide | Z/X | Y/X | NHS-introducing ratio (%) | Self-cross-link-ablity (+/−) | Bond strength (g/cm²) | (Pa) |
|---|---|---|---|---|---|---|---|
| Example 1 | Pectin | 1 | 1 | 25.7 | + | 70 | 6.9 |
| Example 2 | Hyaluronic acid | 1 | 1 | 8.4 | + | 50 | 4.9 |
| Example 3 | CM dextran A | 3 | 10 | 27.7 | + | 85 | 8.3 |
| Example 4 | CM dextran A | 5 | 10 | 29.7 | + | 90 | 8.3 |
| Example 5 | CM dextran A | 10 | 10 | 32.7 | + | 100 | 9.8 |
| Example 6 | CM dextran B | 5 | 10 | 15.3 | + | 120 | 12 |
| Example 7 | CM pullulan | 0.5 | 1 | 7.8 | + | 80 | 7.8 |

(V) Self-crosslinkability of Active Esterified Polysaccharide Derivative

The active esterified polysaccharides obtained in Examples 1 to 7 in (III) were tested for self-crosslinkability.

0.2 g of active esterified polysaccharide was weighed in a 10-mL volume of clean test tube ("Rarubo LT-15100" from Terumo), and 1 mL of pure water was added thereto and mixed. Then, 1 mL of 8.3% (w/v) aqueous solution of sodium hydrogen carbonate (sodium hydrogen carbonate from Wako Pure Chemical Industries, Ltd.) as a pH adjusting agent was added and mixed at about 2,000 rpm for about 1 minute by using a test tube mixer (MT-31 from Yamato Scientific Co., Ltd.). The state of the content of the test tube was visually observed before and after mixing. One which has fluidity after mixing same as the content of the test tube before mixing was regarded as "without self-crosslinkablility (−)", and one in which the content of the test tube formed an agglomerated matrix (hydrogel) was regarded as "with self-crosslinkability (+)". The results are shown in Table 2 above.

(VI) Adhesion Test of Active Esterified Polysaccharide Derivative

An adhesion test in vitro with a fresh integument (pig skin) taken from a Yorkshire edible pig was carried out to determine the adhesion performance of the active esterified polysaccharide derivatives obtained in Examples 1 to 7.

A strip specimen with 1 cm in width by 5 cm in length was cut out from the pig skin. The dermis of the pig skin was exposed, and the exposed surface was used as the adherend. The area of adhesion was defined with 1 cm by 1 cm. To the adherend was applied 100 µL of solution prepared by dissolving 0.2 weighed of the active esterified polysaccharide obtained in Examples 1 to 7 in 1 mL of pure water, and was further applied 10 µL of 8.3% (w/v) aqueous solution of sodium hydrogen carbonate, followed by mixing them. On the adherend, another pig skin strip was placed and loaded with 50 gf/cm$^2$ (ca. 4.9 Pa) for 1 minute. After standing for 5 minutes, the adhesion test was carried out by pulling two-adhered sheets of pig skin strip in the longitudinal direction and in opposite direction with one another at a cross-head speed of 100 mm/min by using a autograph (tensile tester). The tensile strength required to peel off the two pig skin strips was regarded as the adhesive strength. The results are shown in Table 2.

The same experiments as in Examples 1 to 7 were repeated except that 8.3% (w/v) aqueous solution of sodium hydrogen carbonate (pH 8.3) (sodium hydrogen carbonate from Wako Pure Chemical Industries, Ltd.) was replaced by 1 mol/L aqueous solution of disodium phosphate (pH 9.1) (disodium phosphate from Wako Pure Chemical Industries, Ltd.). In result, all of that obtained in examples 1 to 7 possessed self-crosslinkability (+).

The same experiments as in Examples 5 and 7 were repeated except that 10 µL of 8.3% (w/v) aqueous solution of sodium hydrogen carbonate was replaced by 10 µL of 1 mol/L aqueous solution of disodium phosphate (pH 9.1). In result, the adhesive strength of ones that obtained in examples 5 and 7 were 115 g/cm$^2$=11.3 Pa and 95 g/cm$^2$=9.4 Pa, respectively.

(VII) Preparation of Polysaccharide Composition

To an active esterified polysaccharide derivative was added a polymer (C) to prepare a polysaccharide composition.

Example 8

Active Esterified Pectin Composition 1

0.2 g-weighed of the active esterified pectin prepared in Example 1 was added in 1 mL of pure water, and mixed to prepare a main solution. Meanwhile, In 1 mL of 8.3% (w/v) aqueous solution of sodium hydrogen carbonate at (pH 8.3) was added 0.2 g weighed of pentaerythritol-type polyethylene glycol (PEG) derivative having a thiol group on four terminals (Sunbrite PTE-10TSH from NOF Corporation, having a weight-average molecular weight of 10,000), and mixed to prepare a associate solution. 1 mL of the main solution and 1 mL of the associate solution were mixed in a test tube to prepare the polysaccharide composition. The polysaccharide composition has fluidity just after mixing of the main solution and the associate solution, however, the content of the test tube formed an agglomerated matrix (hydrogel) after mixing for about 1 minute at about 2,000 rpm by using a test tube mixer.

Example 9

Active Esterified Pectin Composition 2

The active esterified pectin in example 1 was used. The same procedure as in Example 8 was repeated to prepare the polysaccharide composition except that the pentaerythritol-type polyethylene glycol derivative used in example 8 was replaced by glycerol-type polyethylene glycol derivative having an amino group on eight terminals (Sunbrite HGEO-20TEA from NOF Corporation, having a weight-average molecular weight of 10,000).

Example 10

Active Esterified Pectin Composition 3

The active esterified pectin in example 1 was used. The same procedure as in Example 8 was repeated to prepare the polysaccharide composition except that the pentaerythritol-type polyethylene glycol derivative used in example 8 was replaced by bovine serum albumin (from Sigma).

Example 11

Active Esterified Pectin Composition 4

The active esterified pectin in example 1 was used. The same procedure as in Example 8 was repeated to prepare the polysaccharide composition except that the pentaerythritol-type polyethylene glycol derivative used in example 8 was replaced by 0.02 g of pectin (GENU Pectin USP-H from CP Kelco).

Example 12

Active Esterified Dextran A1 Composition 1

In 1 mL of pure water was added 0.2 g-weighed of the active esterified dextran A1 prepared in Example 3, and mixed to prepare a main solution. Meanwhile, in 1 mL of 8.3% (w/v) aqueous solution of sodium hydrogen carbonate (pH 8.3) was added 0.2 g-weighed of pentaerythritol-type polyethylene glycol (PEG) derivative having a thiol group on four terminals (with a weight-average molecular weight of 20,000) (see, Poly (ethylene Glycol) Chemistry: Biotechnical and Biomedical Applications, compiled by J. Milton Harris, Plenum Press, NY (1992)), and mixed to prepare a associate solution. 1 mL of the main solution and 1 mL of the associate solution were mixed in a test tube to prepare the polysaccharide composition. The polysaccharide composition has fluidity just after mixing of the main solution and the associate solution, however, the content of the test tube formed an agglomerated matrix (hydrogel) after mixing for about 1 minute at about 2,000 rpm by using a test tube mixer.

Example 13

Active Esterified Dextran A1 Composition 2

In 1 mL of pure water was added 0.2 g-weighed of the active esterified dextran A1 prepared in Example 3, and mixed to prepare a main solution. Meanwhile, in 1 mL of 8.3% (w/v) aqueous solution of sodium hydrogen carbonate (pH 8.3) was added 0.2 g-weighed of pentaerythritol-type polyethylene glycol (PEG) derivative having an amino group on four terminals (with a weight-average molecular weight of 10,000) (see, Poly (ethylene Glycol) Chemistry: Biotechnical and Biomedical Applications, compiled by J. Milton Harris, Plenum Press, NY (1992)), and mixed to prepare a associate solution. 1 mL of the main solution and 1 mL of the associate solution were mixed in a test tube to prepare the polysaccharide composition. The polysaccharide composition has fluidity just after mixing of the main solution and the associate solution, however, the content of the test tube formed an agglomerated matrix (hydrogel) after mixing for about 1 minute at about 2,000 rpm by using a test tube mixer.

Example 14

Active Esterified Dextran A1 Composition 3

In 1 mL of pure water was added 0.2 g-weighed of the active esterified dextran A1 prepared in Example 3, and mixed to prepare a main solution. Meanwhile, in 1 mL of 8.3% (w/v) aqueous solution of sodium hydrogen carbonate (pH 8.3) was added 0.2 g-weighed of pentaerythritol-type polyethylene glycol (PEG) derivative having an amino group on four terminals (with a weight-average molecular weight of 20,000) (see, Poly (ethylene Glycol) Chemistry: Biotechnical and Biomedical Applications, compiled by J. Milton Harris, Plenum Press, NY (1992)), and mixed to prepare a associate solution. 1 mL of the main solution and 1 mL of the associate solution were mixed in a test tube to prepare the polysaccharide composition. The polysaccharide composition has fluidity just after mixing of the main solution and the associate solution, however, the content of the test tube formed an agglomerated matrix (hydrogel) after mixing for about 1 minute at about 2,000 rpm by using a test tube mixer.

Example 15

Active Esterified Pullulan Composition

In 1 mL of pure water was added 0.2 g-weighed of the active esterified pullulan prepared in Example 7, and mixed to prepare a main solution. Meanwhile, in 1 mL of 8.3% (w/v) aqueous solution of sodium hydrogen carbonate (pH 8.3) was added 0.2 g-weighed of pentaerythritol-type polyethylene glycol (PEG) derivative having an amino group on four terminals (with a weight-average molecular weight of 20,000) (see, Poly (ethylene Glycol) Chemistry: Biotechnical and Biomedical Applications, compiled by J. Milton Harris, Plenum Press, NY (1992)), and mixed to prepare a associate solution. 1 mL of the main solution and 1 mL of the associate solution were mixed in a test tube to prepare the polysaccharide composition. The polysaccharide composition has fluidity just after mixing of the main solution and the associate solution, however, the content of the test tube formed an agglomerated matrix (hydrogel) after mixing for about 1 minute at about 2,000 rpm by using a test tube mixer.

(VIII) Adhesion Test (1) of Active Esterified Polysaccharide Composition

In order to determine the adhesivility of the polysaccharide compositions prepared in Examples 8 to 11, an adhesion test was carried out in vitro in the same way as in (VI). For the active esterified polysaccharide compositions obtained in Examples 8 to 11, the adhesion test was carried out by applying 50 μL of the main solution and 50 μL of the associate solution on the adherend, and mixing them. The results are shown in Table 3 below.

TABLE 3

| | Active esterified polysaccharide derivative | | Bond strength | |
|---|---|---|---|---|
| | | | g/cm$^2$ | Pa |
| | From Example 1 | Example 8 | 82 | 8.0 |
| Example 9 | From Example 1 | Glycerol-type PEG derivative | 105 | 10 |
| Example 10 | From Example 1 | Bovine serum albumin | 120 | 12 |
| Example 11 | From Example 1 | Pectin | 98 | 9.6 |

(VIII) Adhesion Test (2) of Active Esterified Polysaccharide Composition

In order to determine the adhesivility of the polysaccharide compositions prepared in Examples 12 to 15, an adhesion test was carried out in vitro in the same way as in (VI). For the active esterified polysaccharide compositions obtained in Examples 12 to 15, the adhesion test was carried out by applying 50 μL of the main solution and 50 μL of the associate solution on the adherend, and mixing them. The results are shown in Table 4 below.

TABLE 4

| | Active esterified polysaccharide derivative | Polymer added | adhesive strength | |
|---|---|---|---|---|
| | | | (g/cm$^2$) | (Pa) |
| Example 12 | Example 3 | Pentaerythritol-type PEG derivative having a thiol group on four terminals (with a weight average molecular weight of 20,000) | 103 | 10.1 |
| Example 13 | Example 4 | Pentaerythritol-type PEG derivative having an amino group on four terminals (with a weight average molecular weight of 10,000) | 86 | 8.4 |
| Example 14 | Example 5 | Pentaerythritol-type PEG derivative having an amino group on four terminals (with a weight average molecular weight of 20,000) | 98 | 9.6 |
| Example 15 | Example 7 | Pentaerythritol-type PEG derivative having an amino group on four terminals (with a weight average molecular weight of 20,000) | 128 | 12.6 |

(IX) Preparation of Medical Treatment Material

Example 16

(1) Liquid Medical Treatment Material 1 Containing Active Esterified Pectin

In 1 mL of pure water was added 0.2 g of active esterified pectin obtained in Example 1, and mixed to form a aqueous solution as a main solution. An 8.3% (w/v) aqueous solution of sodium hydrogen carbonate was used as the pH adjusting solution. A liquid medical treatment material 1 which composed of the main solution and the pH adjusting solution was prepared. The main solution and the pH adjusting solution may be used by mixing them at the applying site.

Example 17

(2) Liquid Medical Treatment Material 2 Containing Active Esterified Pectin

In 1 mL of pure water was added 0.2 .g-weighed of active esterified pectin obtained in Example 1, and mixed to form a aqueous solution as a main solution. Meanwhile, in 1 mL of 8.3% (w/v) aqueous solution of sodium hydrogen carbonate was added 0.2 g-weighed of the pentaerythritol-type polyethylene glycol derivative having a thiol group on four terminals, and mixed to form a aqueous solution as a associate solution. A liquid medical treatment material 2 which composed of the main solution and the associate solution was prepared. The main solution and the associate solution may be used by mixing them at the applying site.

Example 18

(3) Powdery Medical Treatment Material Containing Active Esterified CM Dextran A1

A powdery medical treatment material was prepared by mixing from 0.5 g of powder obtained by freeze-crushing the active esterified CM dextran Aobtained in Example 3 and 0.05 g of sodium hydrogen carbonate in powder form. This medical treatment material can be applied to the application site by dusting and mixing them.

Example 19

(4) Powdery Medical Treatment Material Kit Containing Active Esterified CM Dextran A1

A powdery medical treatment material kit was prepared, which was composed of 0.5 g of powder obtained by freeze-crushing the active esterified CM dextran A1 obtained in Example 3 and 100 µL of 8.3% (w/v) aqueous solution of sodium hydrogen carbonate otherwise prepared. This medical treatment material kit can be applied to the application site by dusting and mixing them

Example 20

(5) Sheet-like Medical Treatment Material and Kit 1 Containing Active Esterified Pectin 30 mL of 5% (w/v) aqueous solution of the active esterified pectin obtained in Example 1 was prepared and spread on a plastic dish with 5 cm×5 cm, followed by being frozen at −50° C. in a deep freezer and then dried in remaining its frozen state under reduced pressure using a vacuum dryer. Thus there was obtained a sheet-like medical treatment material with about 5 mm thick. In addition, 1 mL of 8.3% (w/v) aqueous solution of sodium hydrogen carbonate otherwise prepared was composed with the sheet-like medical treatment material to set up a sheet-like medical treatment material kit (1). The sheet-like medical treatment material may be put on the application site and the 8.3% (w/v) aqueous solution of sodium hydrogen carbonate is applied thereon.

Example 21

(6) Sheet-like Medical Treatment Material and Kit 2 Containing Active Esterified Pectin The sheet-like medical treatment material prepared in Example 20 was used. A coating solution was prepared by dissolving 5 g of glycerol-type polyethylene glycol derivative having an amino group on eight terminals in 100 mL of chloroform (from Wako Puke Chemical Industries, Ltd.). The sheet-like medical treatment material prepared in Example 20 was immersed in the coating solution for 1 minute, followed by air drying at 25° C. for 3 hours. Thus there was obtained a sheet-like medical treatment material comprising the active esterified pectin and the polysaccharide composition of glycerol-type polyethylene glycol derivative having an amino group on eight terminals. In addition, A sheet-like medical treatment material kit 2 was also prepared which was composed of 1 mL of 8.3% (w/v) aqueous solution of sodium hydrogen carbonate otherwise prepared and the above-mentioned sheet-like medical treatment material. The sheet-like medical treatment material may be put on the application site and the 8.3% (w/v) aqueous solution of sodium hydrogen carbonate is applied thereon.(X) Evaluation test for hemostatic performance by using small animals A rat (Jcl: SD strain, from Clea Japan, Inc.) was subjected to general anesthesia with Nembutal (from Dainabott) administered by intramuscular injection and had its abdomen cut open so that its spleen was exposed. The surface of the spleen was made an incision about 2 mm long with a scalpel so as to make a bleeding model. Evaluation tests of hemostatic performance for medical treatment materials prepared in Examples 16 to 21 were carried out to observe hemorrhagic states three minutes after their application, and resulted in performances of hemostasis in all the medical treatment materials. These medical treatment materials were prepared in a simple manner just before their application, and did not require any special apparatus.

It is designated in Table 2 that the polysaccharide derivatives according to the present invention (Examples 1 to 7) have an adhesive strength ranging form 50 to 120 (g/cm$^2$) within the range 30 to 150 (g/cm$^2$) which is required generally for a hemostatic material and a medical adhesive, and also within the range 50 to 120 (g/cm$^2$) which is suitable for such uses. Likewise, the polysaccharide compositions according to the present invention (Examples 8 to 15) also have an adhesive ranging form 82 to 128 (g/cm$^2$), and are suitable for use as a hemostatic material and a medical adhesive.

The present invention is described in detail by way of examples, below. However, these examples are demonstrated by way an example, thus the present invention is not limited thereto.

INDUSTRIAL APPLICABILITY

The polysaccharide derivative and composition of the present invention, in using as an adhesive for tissues, is a sufficient bond strength that meets clinical requirements. They avoid the risk of infection because they have the backbone of natural or artificial polysaccharide. Their components in themselves or their decomposition products have a low level of toxicity. The polysaccharide derivative of the present invention does not need complex steps for preparation at the time of use. It can be prepared readily and simply without requiring special apparatus at the time of use. The polysaccharide derivative may be provided alone as the polysaccharide composition; therefore, it will find a large variety of uses. Since the polysaccharide composition of the present invention employs the polysaccharide derivative of the present invention, it does not impair the characteristic properties of the present invention.

The polysaccharide derivative and composition of the present invention can be fabricated into powder, sheet, granules, or any other forms. Therefore, they can be used in various ways according to the object of their use. The polysaccharide derivative and composition of the present invention can be produced simply by mixing with heating necessary reagents, without requiring special apparatus. Owing to the above-mentioned characteristic properties, the polysaccharide derivative and composition of the present invention are suitable for use as the medical treatment material such as hemostatic agent and adhesive.

The invention claim is:

1. A crosslinkable polysaceharide composition comprising an uncrosslinked polysaceharide derivative (A) and a pH adjusting agent (B),
    wherein said polysaceharide derivative (A) has at least one active ester group containing a N-hydroxylamine-based electrophilic moiety which is introduced to a carboxy group at a side chain of the acid-containing polysaceharide, and may form a covalent bond through a reaction with an active hydrogen-containing group selected from the group consisting of a hydroxy group, an amino group, and a thiol group under alkaline conditions in the presence of moisture, and
    which is a powder mixture comprising the polysaceharide derivative (A) and the pH adjusting agent (B).

2. The composition according to claim 1, which further comprises a polymer other than said polysaceharide derivative (A).

3. A medical treatment material which comprises the composition according to claim 1.

4. The medical treatment material according to claim 3, which is a hemostatic agent and/or biomedical adhesive.

* * * * *